United States Patent [19]

Ninomiya et al.

[11] Patent Number: 4,654,583
[45] Date of Patent: Mar. 31, 1987

[54] METHOD AND APPARATUS FOR DETECTING DEFECTS OF PRINTED CIRCUIT PATTERNS

[75] Inventors: Takanori Ninomiya, Yokohama; Yasuo Nakagawa, Chigasaki; Keiya Saito, Yokohama, all of Japan

[73] Assignee: Hitachi, Ltd., Tokyo, Japan

[21] Appl. No.: 600,957

[22] Filed: Apr. 16, 1984

[30] Foreign Application Priority Data

Apr. 15, 1983 [JP] Japan ................................ 58-65659
Aug. 25, 1983 [JP] Japan ................................ 58-154060

[51] Int. Cl.⁴ ...................... G01R 15/12; G01B 11/00
[52] U.S. Cl. .................................. 324/73 PC; 356/394
[58] Field of Search .............................. 356/394, 398; 324/73 PC, 73 R, 158 R; 382/47; 358/106, 107

[56] References Cited

U.S. PATENT DOCUMENTS 3,976,864 8/1976 Gordon et al. ................... 324/73 R
4,153,896 5/1979 White ................................. 382/47
4,508,453 4/1985 Hara et al. ........................ 356/394

Primary Examiner—Ernest F. Karlsen
Assistant Examiner—Vinh P. Nguyen
Attorney, Agent, or Firm—Antonelli, Terry & Wands

[57] ABSTRACT

A printed circuit pattern inspection system, in which the optical image of circuit patterns is transformed into an electrical signal, the signal is converted into a binary digital signal, the connectivity relationship between selected two points of pattern in the form of binary signal is examined, connection data representative of the connectivity relationship and expressed by a pair of numbers given to the points is generated, and the connection data is compared with design data which is produced from design information and expressed in the form of a circulation list of numbers given to points in linkage relationship, whereby determination of defectiveness of patterns is made basing on the result of comparison.

22 Claims, 67 Drawing Figures

FIG. 1A
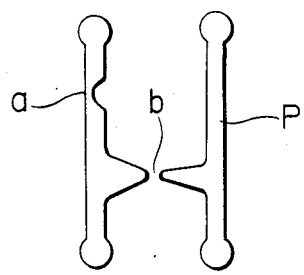
FIG. 1B
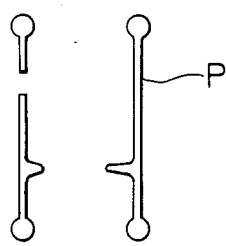
FIG. 1C
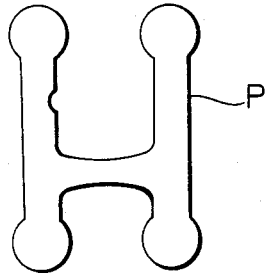
FIG. 2
| OBJECT PAD NUMBER | MOTHER PAD NUMBER |
|---|---|
| | |
FIG. 3A
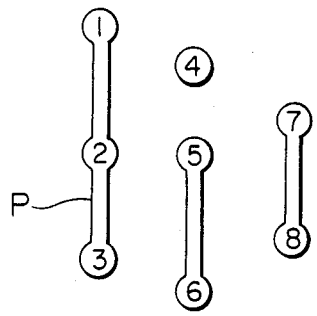
FIG. 3B
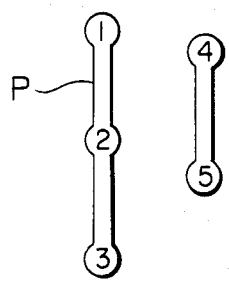

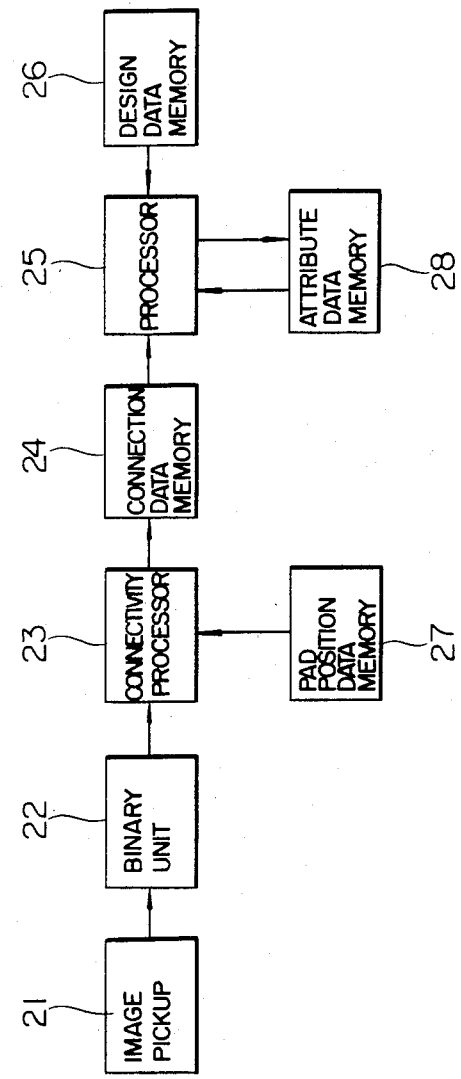

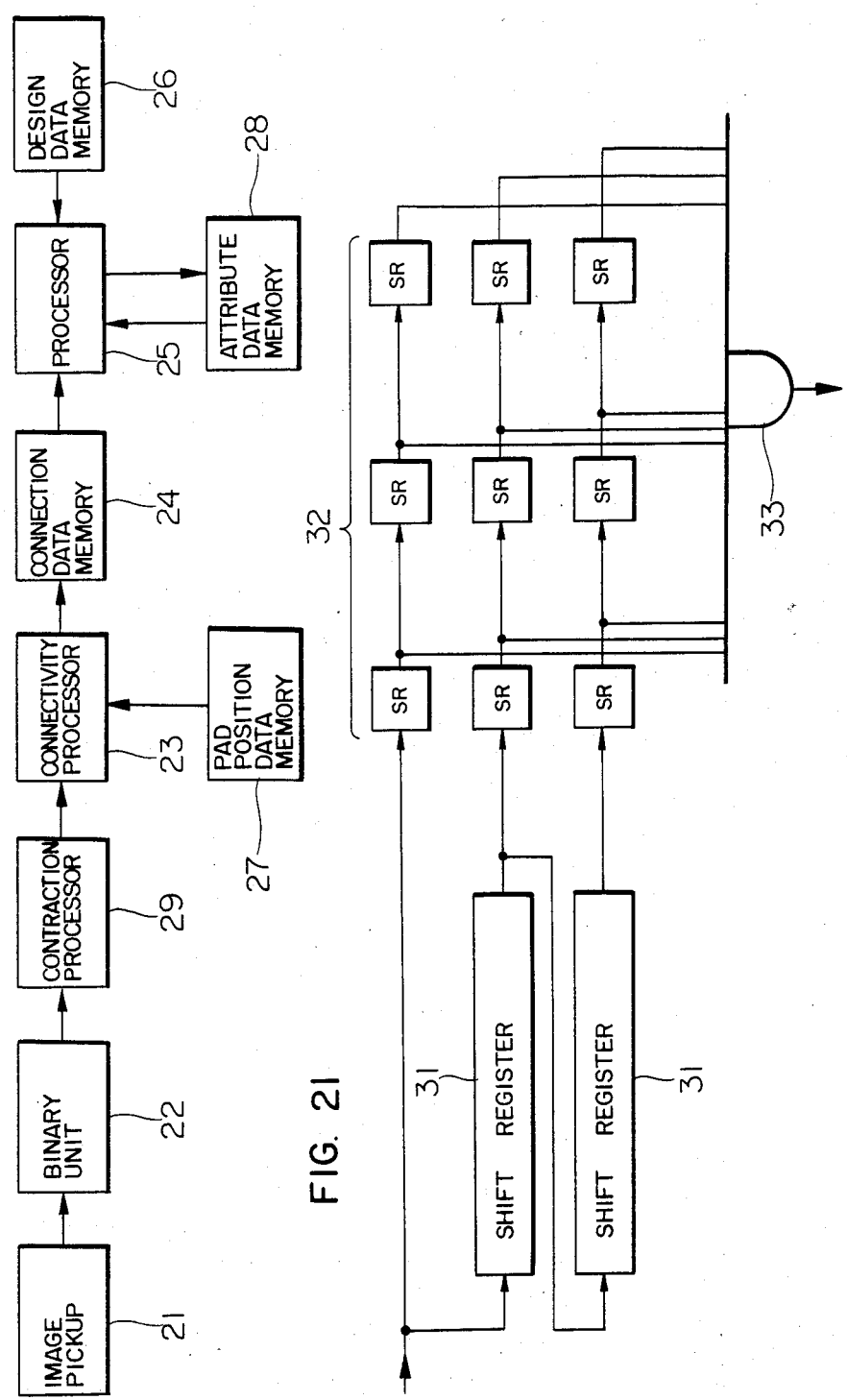

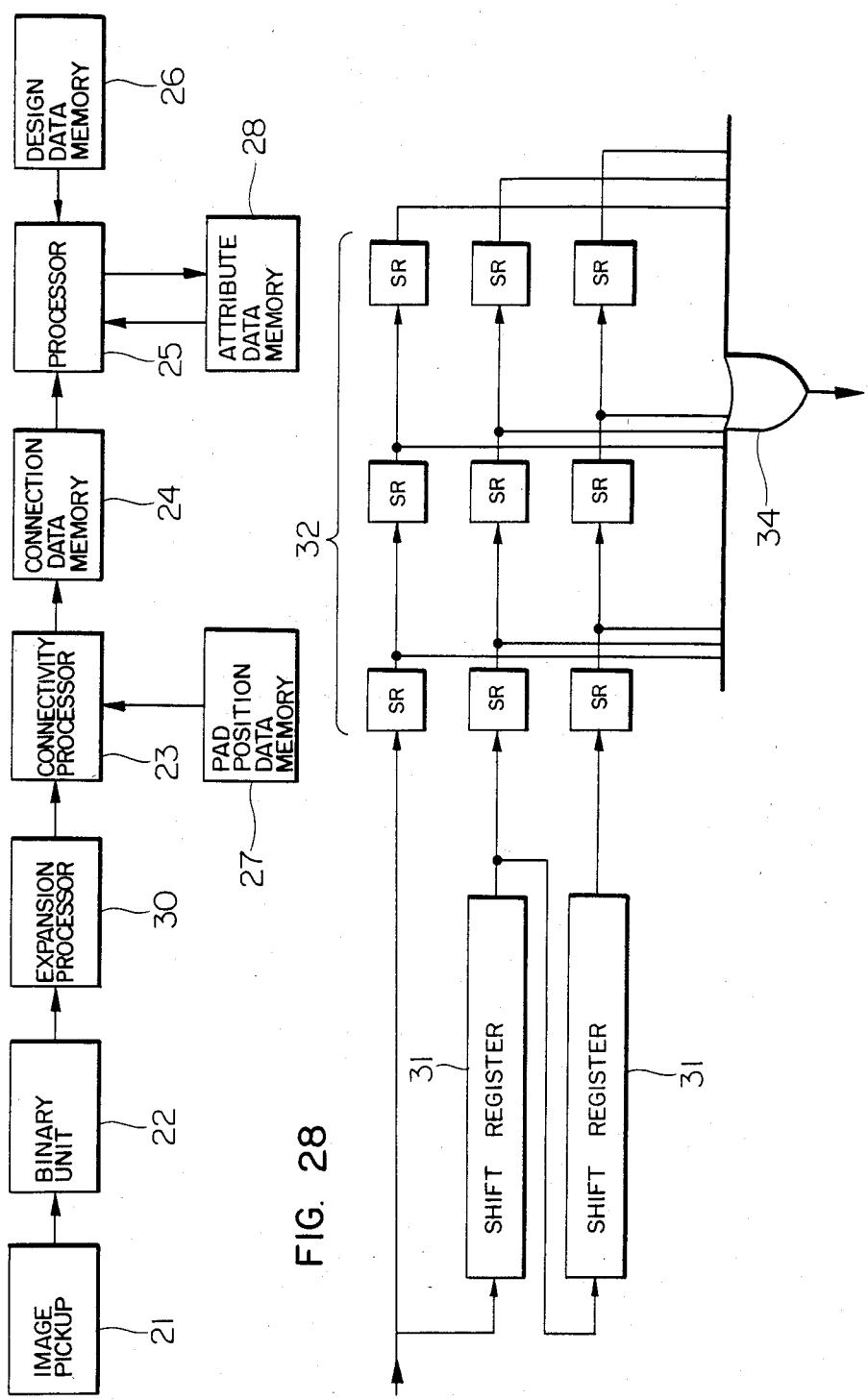

METHOD AND APPARATUS FOR DETECTING DEFECTS OF PRINTED CIRCUIT PATTERNS

The present invention relates to a method and apparatus for detecting defects of printed circuit patterns such as, for example, green sheet patterns, the method and apparatus being particularly suitable for detecting defective patterns related to the electrical conduction in a fast, non-contact manner.

There has been used a printed circuit pattern inspection system, in which specific pad positions are memorized in advance and a voltage is applied between two pad positions through a pair of contact probes so as to discriminate the conduction and line breakage or the isolation and short-circuit based on the presence or absence or the magnitude of the current flowing through the contact probes. This system, however, requires direct contact of the probes to the circuit patterns and, therefore, has many shortcomings such as the low reliability of inspection due to the variation of contact resistance, the wear of contact probes, the need of probe replacement when it is broken, and the creation of damage or in the worst case breakage of circuit patterns by the inappropriate contact operation. In addition, if a circuit pattern includes a narrow section or if two patterns are placed too close, the concentration of the current or electric field to these sections can possibly affect the long term reliability of the printed circuit, and it is very difficult for the above-mentioned conventional system to detect such defective circuit patterns.

Another conventional system for inspecting printed circuit patterns is the non-contact detection through the optical image of circuit patterns. This system has several versions including the comparison of patterns under test with designed patterns, the comparison of two circuit patterns to be inspected (as disclosed for example in U.S. Pat. No. 4,148,065), and the detection of the presence and absence of partial patterns which are especially material based on design information. These subsystems are based on the judgement criterion whether or not patterns of correct dimensions are located at specified positions, and for a printed circuit pattern where defects are to be determined from the conductive characteristics and large deviation of pattern dimensions, many tolerable cases would be detected as defects, resulting in a serious problem of the inspection efficiency.

It is an object of the present invention to overcome the foregoing prior art deficiencies and provide a method and apparatus for detecting defects of printed circuit patterns such as line breakage, short-circuit, extremely narrow pattern section, and extremely small spacing of patterns, in a fast, non-contact manner.

In order to achieve the above objective, the present invention resides in the detection of defective circuit patterns, wherein optical images of circuit patterns are transduced into an electrical signal, the signal is transformed into a binary signal, the connectivity between two selected points of the binary patterns is examined, the examination result is formed into connection data expressed by a pair of symbols (numbers) given to the test points, and the connection data is compared with design data expressed by symbols (numbers) in the form of a circulation list given to points in connection created from design information, thereby to detect a defect of printed circuit patterns.

According to one preferable form of the present invention, a contraction process and/or expansion process for binary patterns is added between the binary digitizing process for the electrical signal and the connection data forming process, so that determination of a defect is made on the basis of the results obtained through the additional processes, or on the basis of the results of the additional processes taking into account the result obtained without the additional process.

For detecting the electrical conductivity of circuit patterns in a non-contact manner in consideration that patterns exist on the plane, the optical images of patterns are detected and only conductive portions thereof are extracted in the form of binary patterns. A connectivity process is carried out for the binary patterns to examine the connection between the two binary patterns representative of two pads of a printed circuit. The result of the process is compared with the correct connection data obtained from design information, and the inspection for line breakage and short-circuit is made possible.

In the case of a pattern P as shown in FIGS. 1A–1C, an extremely narrow section of a pattern or an extremely narrow spacing of patterns are forced to become broken or short-circuited by the contraction process (FIG. 1B) or the expansion process (FIG. 1C), respectively, so as to facilitate the detection for such defects. In FIG. 1A, symbol a indicates the extremely narrow section of a pattern, and symbol b indicates the extremely narrow spacing of patterns. These sections appear as a line breakage in FIG. 1B showing patterns which have undergone the contraction process, and as a short-circuit in FIG. 1C showing patterns which have undergone the expansion process.

In the inventive system, output data of the connectivity process is formed into a pair of pads, one being the object pad to which attention is paid currently, while the other being a pad linked with the object pad, and connection data based on design information is formed in a circulation list (in this specification, the former data will be termed "connection data", and the latter data will be termed "design data"), so that each paired data is taken out of connection data for the examination of whether or not each pad pair exists on the circulation list of design data. This system realizes significant reduction in the quantity of data to be processed and the quantity of pro- cessing.

Connection data will further be explained in detail. As shown in FIG. 2, one set of connection data is made up of an object pad symbol (number) and a mother pad number in pair. The pad symbol (number) is a number appended according to a certain rule to a pad which needs to be tested for conductivity and the like on the circuit pattern. For example, pads are numbered in order from top to bottom and from left to right starting from 1 as shown in FIG. 3A. The mother pad is a specific pad which represents one linked circuit pattern, and it is determined according to a certain rule such as, for example, the leftmost pad of a circuit pattern becomes the mother pad. Table 1 shows connection data representing the circuit patterns exemplified in FIG. 3B. In this example, the pads with pad symbols (numbers) 1 and 4 are mother pads. Pairs of pad symbols (numbers) are stored (addressed) in arbitrary order as shown in Table 1.

TABLE 1

| Object pad | Mother pad |
|---|---|
| 2 | 1 |
| 1 | 1 |
| 5 | 4 |
| 3 | 1 |
| 4 | 4 |

Next, design data will further be explained in detail. Design data has a structure of a circulation list, per each pattern, made up of the address, i.e., pad symbol (number) of each pad and the pad symbol (number) of another pad which is in connection with the former pad and appears first when the number representing the pad is varied circularly. Individual circulation list represents the connectivity relationship of all pads existing on one continuous circuit pattern. Here, the connectivity relationship implies solely the linkage relationship between pads and does not show the positional relationship of pads in a geometrical sense. The list is made in the ascending order of the pad symbols (numbers). Table 2 shows the design data produced for the circuit patterns exemplified in FIG. 3B.

TABLE 2

| Address | Pad symbol (number) |
|---|---|
| 1 | 2 |
| 2 | 3 |
| 3 | 1 |
| 4 | 5 |
| 5 | 4 |

The following describes the method of defect detection which is based on the comparison of connection data with design data. For the convenience of storing intermediate process data, 2-bit attribute data is appended to each pad symbol (number), i.e., address, of design data.

The algorithm of defect detection is as follows.

Step 1. All attribute data are reset to zero.

Step 2. All connection data are compared with design data in the following procedures, and the results are set to the attribute data area. If the pad numbers on the same row of connection data are equal, attribute data is set to 1; otherwise, the circulation list of design data is scanned circularly to find if the pad number in the right column (mother pad number) of connection data exists in design data. If it is found, attribute data is set to 2; otherwise, it is set to 3.

Step 3. Attribute data of circulation lists of design data are examined to discriminate the condition of the circuit pattern in accordance with the following criteria.

Case 1. One or more attribute data indicate 0: Defective pad (missing pad)

Case 2. One attribute data indicates 1, with remaining data indicating 2: Normal circuit pattern Case 3. Two or more attribute data indicate 1: Line breakage Case 4. One or more attribute data indicate 3: Short-circuit Step 4. The defect discrimination results for individual circulation lists (linked circuit patterns) are outputted.

The present invention will be described in further detail by way of embodiment with reference to the drawings. The present invention is not limited to the illustrated embodiments, but various changes and modifications are of course possible without departing from the scope of the present invention.

Another feature of the present invention is that patterns formed on a white sheet which disperses the light (e.g., a green sheet mainly made of alumina) using black (or a color darker than the sheet) metallic (e.g., tungsten) fine particles are detected fast and reliably without being affected by the regular reflection light from the pattern surface.

Namely, the present invention resides in the apparatus for detecting patterns formed on a planar surface of an object comprising a means for illuminating the object and a means for transducing the optical image of the illuminated object into an electrical signal, wherein the illuminating means is disposed to illuminate the object from the side on which patterns to be detected are formed, and wherein the apparatus comprises two sets of image pickup means which detect the same portion of the illuminated patterns along optical axes in two different directions on the side of the patterns and transduces the contrastive optical images of the patterns into electrical signals, and a composing means which composes corresponding portions of the patterns in the two electrical signals produced by the image pickup means.

According to one preferable form of the present invention, the image pickup means is a linear sensor and the composing means comprises a means for digitizing the two electrical signals into binary signals separately and a means for taking the logical product or logical sum of the two binary signals, or comprises a means for providing a value corresponding to the larger or smaller of the two electrical signals.

The present invention was made based on the experiences of the inventors, which will be described in the following.

Although the following discussion is entirely devoted to patterns formed of metallic fine particles, the same effect is of course achieved for patterns made of non-metallic fine particles.

The method of pattern detection using a bright field illumination will be described again. FIG. 36A shows, as an example, the cross section of a circuit pattern formed of metallic fine particles, and FIG. 36B is a magnified view of a portion of the fine metallic particles in FIG. 36A. As shown in FIG. 36B, a metallic particle 39 generally has several planes (cleavage planes) 40. Therefore, the regular reflection of illumination rays on the surface of each particle is in accord with the law of reflection, i.e., the incident angle is equal to the reflection angle. FIG. 37 shows this affair, where reference number 41 denotes an incident ray and 42 denotes a reflection ray. Since the cleavage planes of fine particles on the surface of the pattern have individual normal directions at random, the illumination ray projected from above the pattern in one direction makes regular reflection at each point of the pattern in random directions. Therefore, when the background is made of a material which is detected brighter than the pattern P, an incident point of the regular reflection ray at the incident aperture of the focus lens of the optical system is detected as a bright spot on the pattern, resulting in a kind of noise (will be termed "bright spot noise" 35) on the detected image (FIG. 34). If, on the other hand, the background is made of a material which is detected darker than the pattern P, the portion on which the reflection ray is not incident at the incident aperture of the focus lens of the optical system is detected as a dark spot on the pattern, resulting in a kind of noise (will be termed "dark spot noise" 36) on the detected image (FIG. 35).

Taking into account that the regular reflection ray at each point can only be detected along a specific direction, the bright spot noise 35 does not appear in the same direction on the pattern for the detected image taken from two separate directions. In addition, by providing a large numerical aperture for the optical system, the dark spot noise 36 does not appear, in most cases, in the same position on the detected image taken along two separate directions. On this account, by composing the detected images taken along two directions in such a manner that the bright spot noise 35 or dark spot noise 36 is cancelled, pattern detection without including the bright spot noise 35 and dark spot noise 36 is made possible. FIGS. 38A-38D illustrate this principle. FIG. 38A shows the patterns to be detected, FIGS. 38B and 38C show detected images taken along two different directions, and FIG. 38D shows the composed image.

The present invention will become more apparent from the following detailed description taken in conjunction with the accompanying drawings, in which:

FIG. 1A is a plan view of one example of the original pattern;

FIG. 1B is a plan view of the pattern obtained through the contraction process for the pattern shown in FIG. 1A;

FIG. 1C is a plan view of the pattern obtained through the expansion process for the pattern shown in FIG. 1A;

FIG. 2 is a diagram showing the structure of connection data;

FIGS. 3A and 3B are plan views showing two different examples of circuit patterns;

FIG. 4 is a block diagram showing the system arrangement for carrying out the first embodiment of the inventive method;

FIGS. 5A and 5B are plan views of 4-link and 8-link picture elements explaining the connectivity of the inventive processing system;

FIG. 1i is a plan view showing normal patterns corresponding to the patterns under test shown in FIG. 18;

FIG. 20 is a block diagram showing the system arrangement for carrying out the second embodiment of the inventive method;

FIG. 21 is a block diagram showing the arrangement of the contraction processor;

FIG. 27 is a block diagram showing the system arrangement for carrying out the fourth embodiment of the inventive method;

Figure 22:
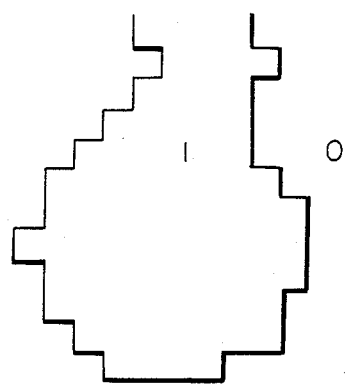
FIG. 22 is an illustration showing one example of binary pattern.
Figure 24:
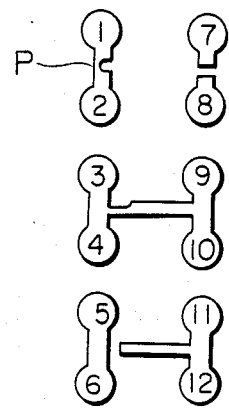
FIG. 24 is a plan view of another example of patterns under test.
Figure 29:
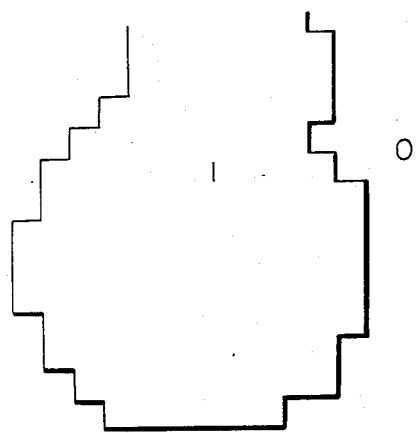
Figure 30:
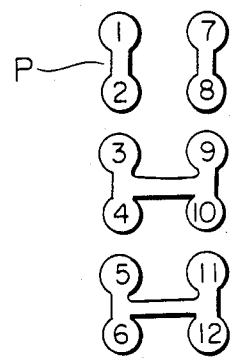
Figure 31:
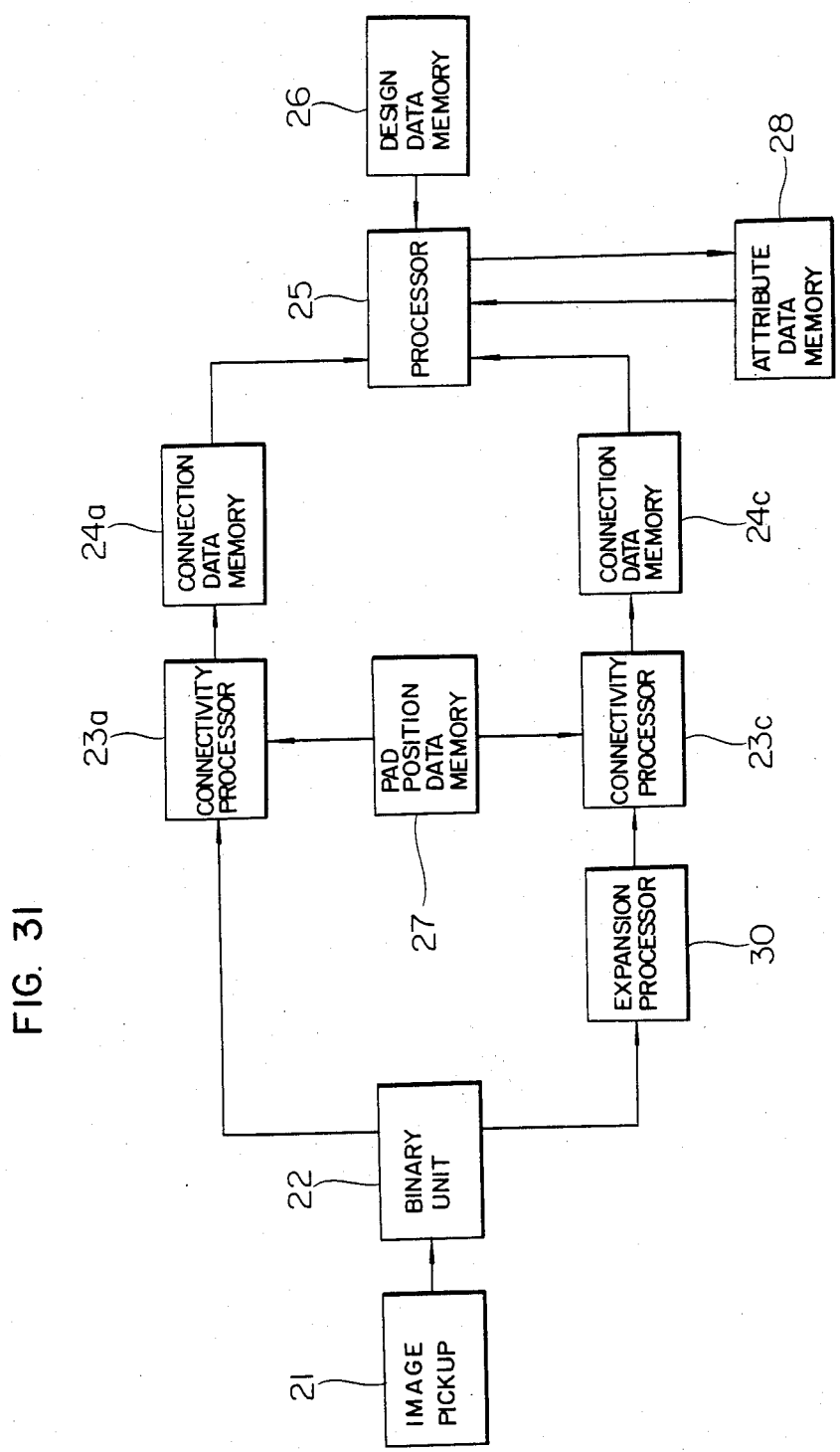
Figure 32:
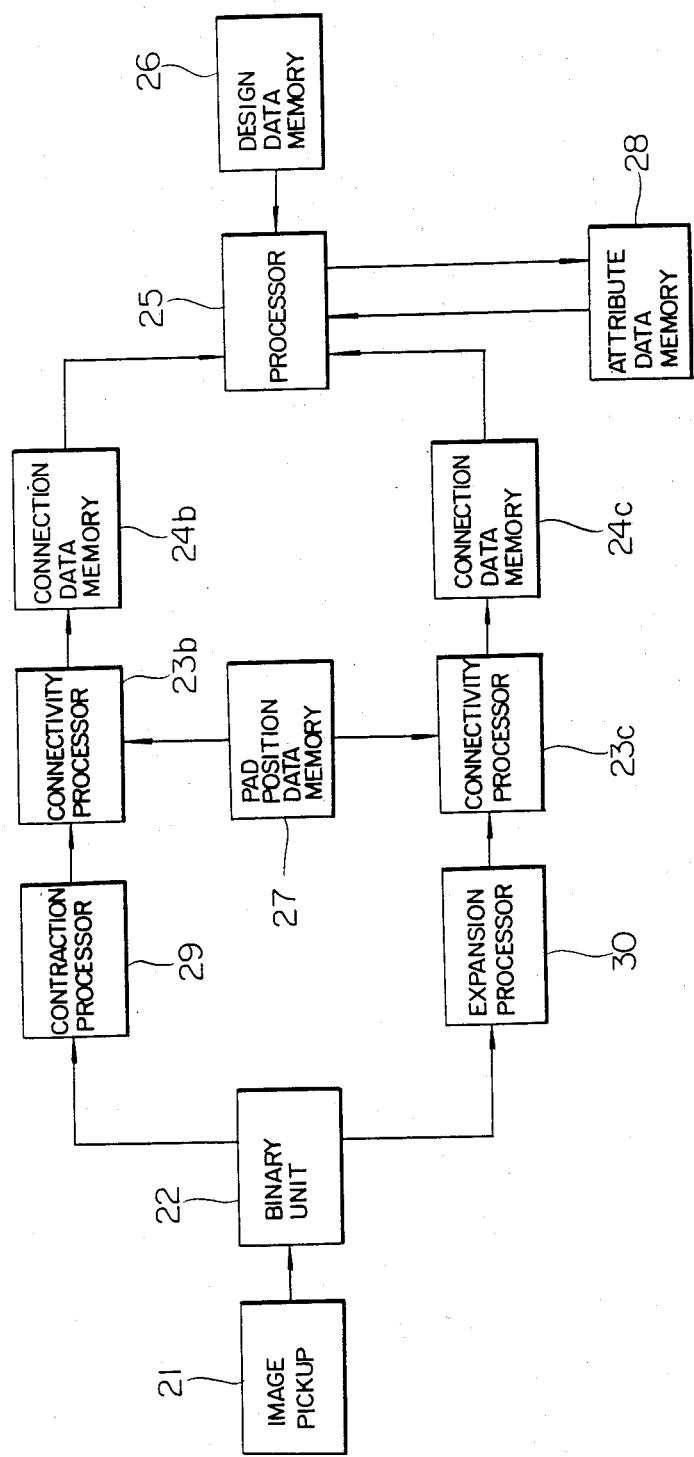
Figure 33:
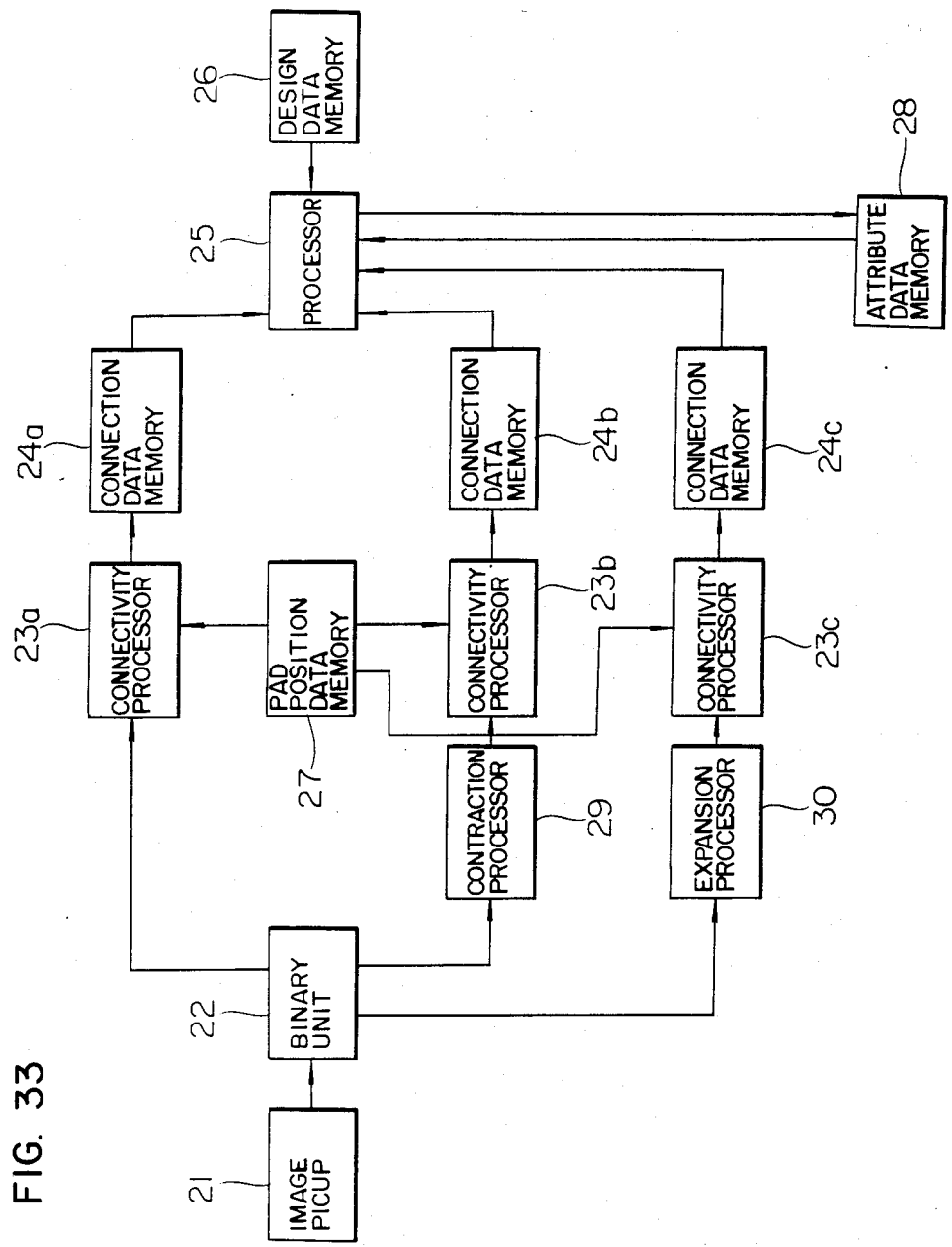
Figure 34:
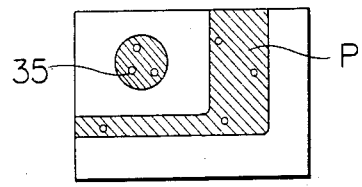
Figure 35:
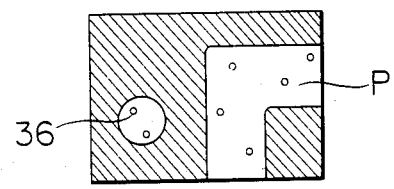
Figure 36A:
Figure 36B:
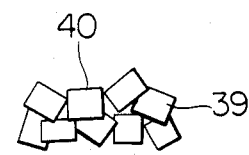
Figure 37:
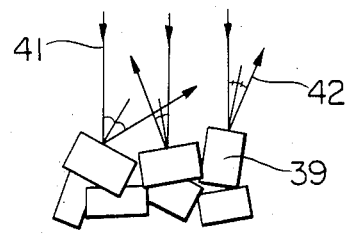
Figure 38A:
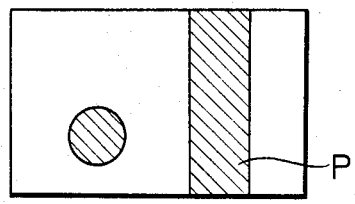
Figure 38B:
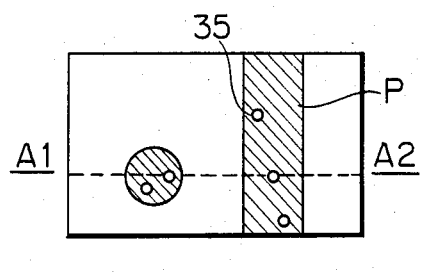
Figure 38C:
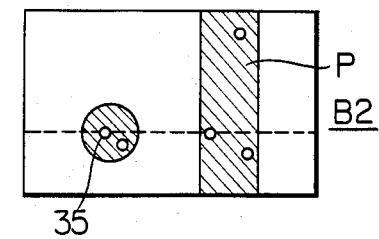
Figure 38D:
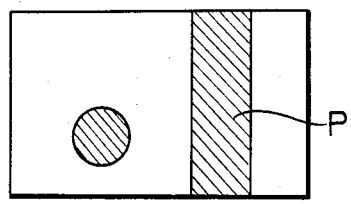
Figure 39:
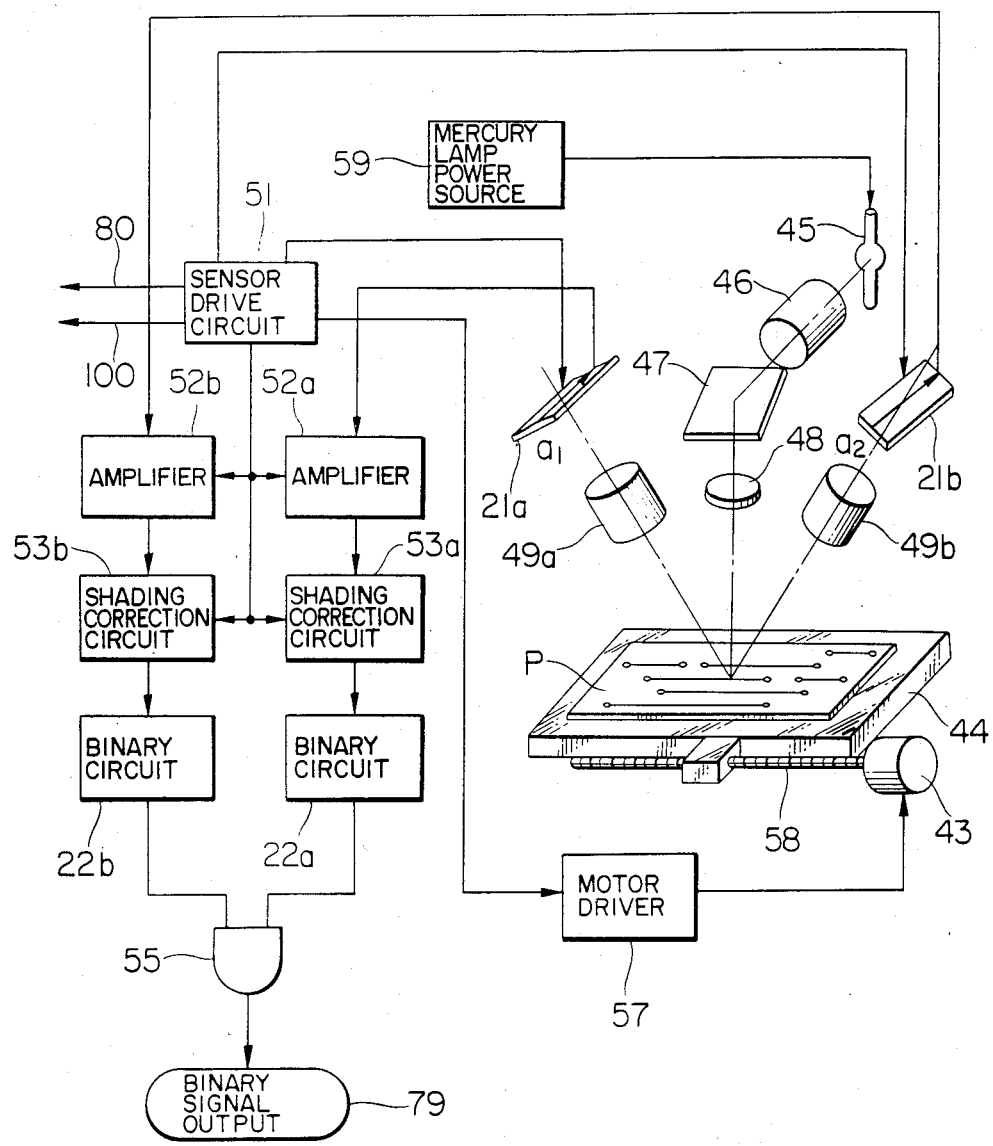
Figure 40A:
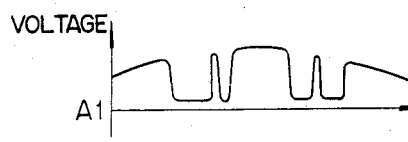
Figure 40A:
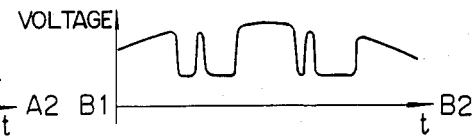
Figure 40B:
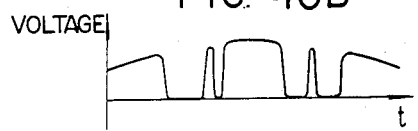
Figure 40B:
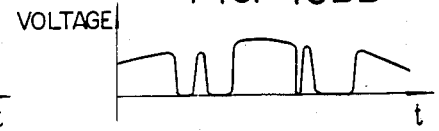
Figure 40C:
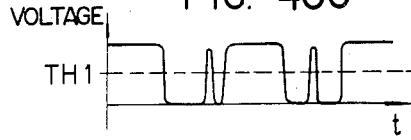
Figure 40C:
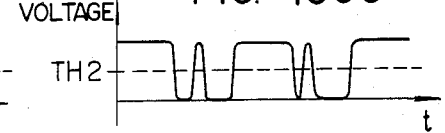
Figure 40D:
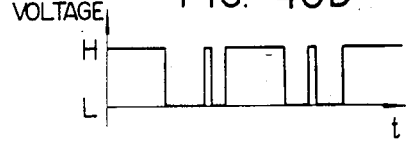
Figure 40D:
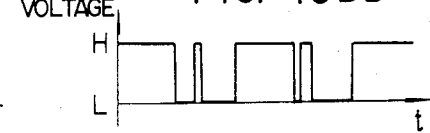
Figure 40E:
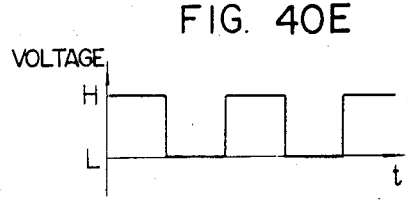
Figure 41:
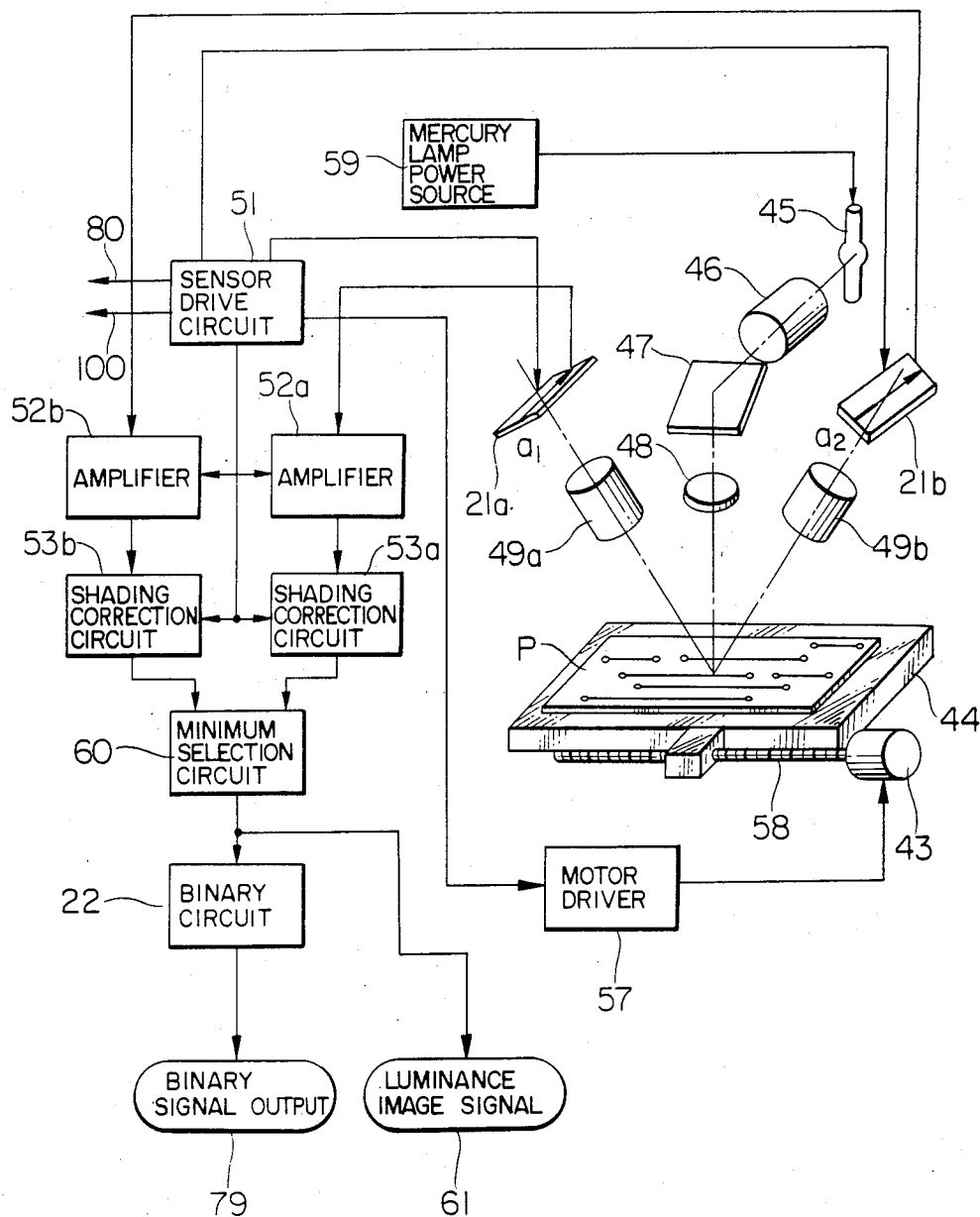

FIG. 28. is a block diagram showing the expansion processor;

FIG. 29 is an illustration showing a pattern obtained through the expansion process for the pattern shown in FIG. 22;

FIG. 30 is a plan view of a pattern obtained through the expansion process for the pattern shown in FIG. 24;

FIGS. 31, 32 and 33 are block diagrams showing the system arrangements for carrying out the fifth, sixth and seventh embodiments of the inventive method;

FIGS. 34 and 35 are illustrations showing noises appearing on the detected images of circuit patterns made of metallic fine particles;

FIGS. 36A and 36B are cross-sectional view and its partial magnified view showing the pattern formed of metallic fine particles;

FIG. 37 is an illustration showing the directions of light reflection on the pattern;

FIGS. 38A-38D are diagrams used to explain the principle of the present invention;

FIGS. 39 and 41 are block diagrams showing different embodiments of the inventive pattern detection apparatus; and FIGS. 40A-40E, 40AA-40DD and FIGS. 42A-42E, 42AA-42CC are waveform diagrams used to explain the operation of the apparatus shown in FIGS. 39 and 41, respectively.

First, an embodiment representing the most fundamental version of the inventive method will be described. FIG. 4 shows the system arrangement for carrying out this embodiment. In the diagram, an image pickup unit 21 operates to transduce the optical image of patterns under test into the electrical signal. The image pickup unit 21 may be a 2-dimensional image pickup apparatus such as a TV camera, or may be the combination of a linear sensor and a one-way drive mechanism. The electrical signal is transformed into a binary digital signal (binary pattern) by means of a binary digitizing circuit 22. The binary digitizing system may be of a fixed threshold type, a floating threshold type which provides the stability in generating binary image patterns, or a means of shading correction. The binary signal is supplied to a connectivity processor 23 which produces connection data as shown in FIG. 2. In order to provide the pad number for the connectivity process, data representing the correspondence between the pad position and the pad number is prepared in advance based on design information and stored in the pad position data memory 27. The connectivity processor may be the system disclosed in Japanese Patent Laid-open No. 53-79571, or one as will be described in the following.

Figure 8:
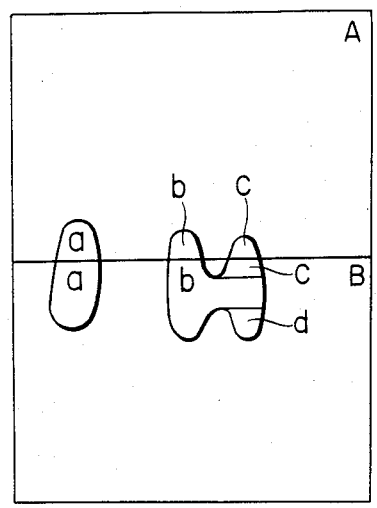
FIG. 8 is a plan view used to explain the management of the pattern number at the boundary of the upper and lower detection fields.

The connectivity of binary patterns formed by the binary signal provided by the digitizing circuit 22 may be of 4-link as shown in FIG. 5A or 8-link as shown in FIG. 5B, or may be defined in another way. Each square shown in FIGS. 5A and 5B represents a picture element. FIG. 5A shows that the object picture element located at the center is assumed to link with four picture elements of the same value located above, below, right and left with respect to the object picture element, while FIG. 5B shows that the object picture element in the center is assumed to link with eight picture elements including the above-mentioned four picture elements plus four picture elements located in the oblique directions with respect to the object picture element.

Figure 6:
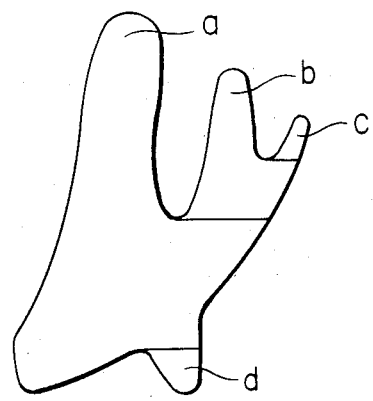
FIG. 6 is a plan view illustrating patterns used to explain the pattern number and link number.

In detecting a pattern defined by a closed curve as shown in FIG. 6 through the above-mentioned sequential scanning, a convex section at the top left appears first, then a middle convex section appears, and finally a convex section at the top right appears. At a time when each convex section is detected, it is not known that these three sections link with one another and, therefore, these sections are given individual pattern numbers in the order of detection, e.g., a, b and c. These sections are also given link numbers a, b and c at the same time. That is, when patterns are detected as isolated patterns, their pattern numbers are used automatically as link numbers. As the scanning detection proceeds, it is found that pattern b (a pattern with pattern number b) is in linkage with pattern c, and at this time point, the link number of pattern c is changed to b. Namely, when two patterns are found to join, the link numbers of these patterns are unified to the smaller number at that time. Accordingly, as the scanning detection further proceeds and when patterns a and b are found to join, the link numbers of patterns b and c are changed to a. When a pattern is found to branch as shown at the bottom of FIG. 6, the branching pattern, i.e., the right-hand pattern section, is given a new pattern number, i.e., d in this example, and pattern d has the common link number a. In this way, by extracting patterns with the same link number a for the case of a pattern shown in FIG. 6 upon completion of the connectivity process for one detection field, pad number data for the whole isolated pattern can be obtained.

Figure 7:
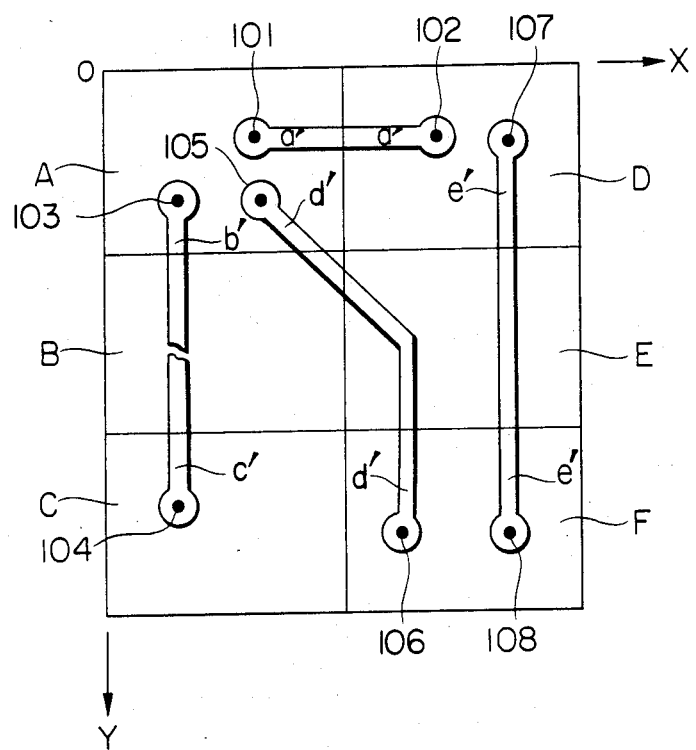
FIG. 7 is a plan view showing patterns in a plurality of split detection fields.
Figure 9:
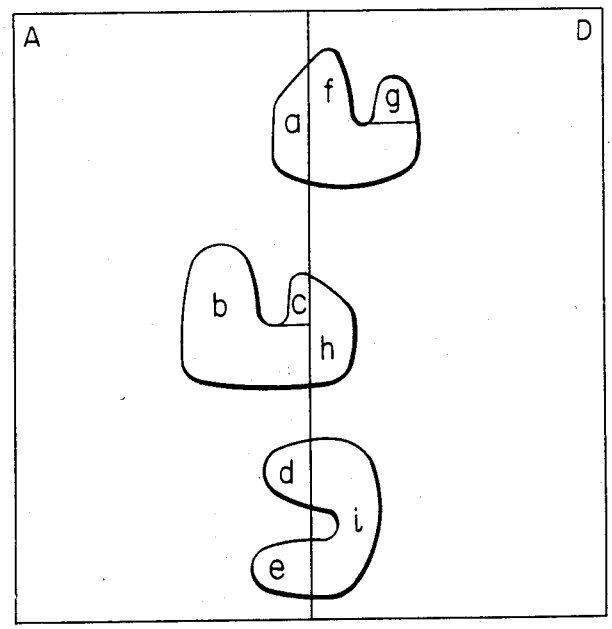
FIG. 9 is a plan view used to explain the management of the pattern number at the boundary of the right-hand and left-hand detection fields.

FIG. 7 shows an example of patterns appearing in a plurality of split detection fields, and these patterns are formed on the green sheet. When the automatic inspection is conducted to detect small defects of patterns on such a large green sheet, it often becomes necessary to divide the field into a plurality of split detection fields due to the limit of resolution of the image pickup unit. In the example of FIG. 7, the whole object area is divided into six split detection fields A through F for the defect detecting operation. It is assumed here that the sequence of detection is in the order of A, B, C, D, E and F, i.e., from top to bottom and then from left to right. In this case a serial pattern number and link number are used for all detection fields, and for a pattern across the boundary of the upper and lower fields A and B as in FIG. 8, common pattern numbers e.g., a, b and c, are given, while for a pattern across the boundary of the right-hand and left-hand fields A and D as in FIG. 9, separate pattern numbers are given. In the example of FIG. 9 with the processing being conducted for the right-hand detection field D, when a pattern first appears at the top left, pattern number f and link number f are given to the pattern, then a convex pattern section which appears next is given pattern number g and link number g, and when the patterns f and g are found to join, the link number of pattern g is changed to f, and finally when the connection of pattern a in the left-hand field to pattern f is completed, the link numbers of patterns f and g are changed to a which is the link number for pattern a. For the next pattern h, link number h is given initially, and when the connection of this pattern with pattern C in the left-hand field is completed, the link number of pattern h is changed to b which is the revised link number for pattern C. Subsequently, when the connection of pattern b in the left-hand field with pattern h is completed, link number b of pattern h is compared with link number b of pattern b, and link number b for patterns b and h is left unchanged. For pattern i, it is initially given link number i, and when patterns d and i are found to link, the link number of pattern i is changed to d of pattern d, and when the connection of patterns e and i is completed, the link numbers of patterns e and i are compared and link number e of pattern e is changed to d of pattern i, while link number d for pattern i is left unchanged. Accordingly, at the end of the process for the right-hand field D, the three isolated patterns across the boundary of the right-hand and left-hand detection fields have pattern numbers a through i and three link numbers a, b and d.

Next, the connectivity processor for carrying out the foregoing process will be described with reference to FIGS. 10 and 11. In the following description, the detection fields are placed on the coordinates having a horizontal X axis and a vertical Y axis with the origin located at the top left of the first split detection field which is located at the top left of the whole field. The arrangement of the connectivity processor shown generally in block form in FIG. 10 includes an X-axis pattern detector 71, X-axis pattern connectivity processor 72, Y-axis pattern detector 73, Y-axis boundary pattern connectivity processor 74, X-axis pattern register 75, Y-axis pattern register 76, pad number register 77, and register controller 78. In operation, the X-axis pattern detector 71 detects patterns such as those shown in FIGS. 6 and 8 on the X-axis scanning line in the binary signal 79, the X-axis pattern connectivity processor 72 performs the connectivity process for the patterns on the X-axis scanning line, while the Y-axis pattern detector 73 detects patterns such as those shown in FIG. 9 across the boundary in the Y direction of the detection fields in the binary signal 79, and the Y-axis boundary pattern connectivity processor 74 performs the connectivity process for the patterns across the boundary in the Y direction. In addition, the X-axis pattern register 75, Y-axis pattern register 76, pad number register 77, and register controller 78 perform storing of pattern information and control necessary for the foregoing connectivity process.

Figure 10:
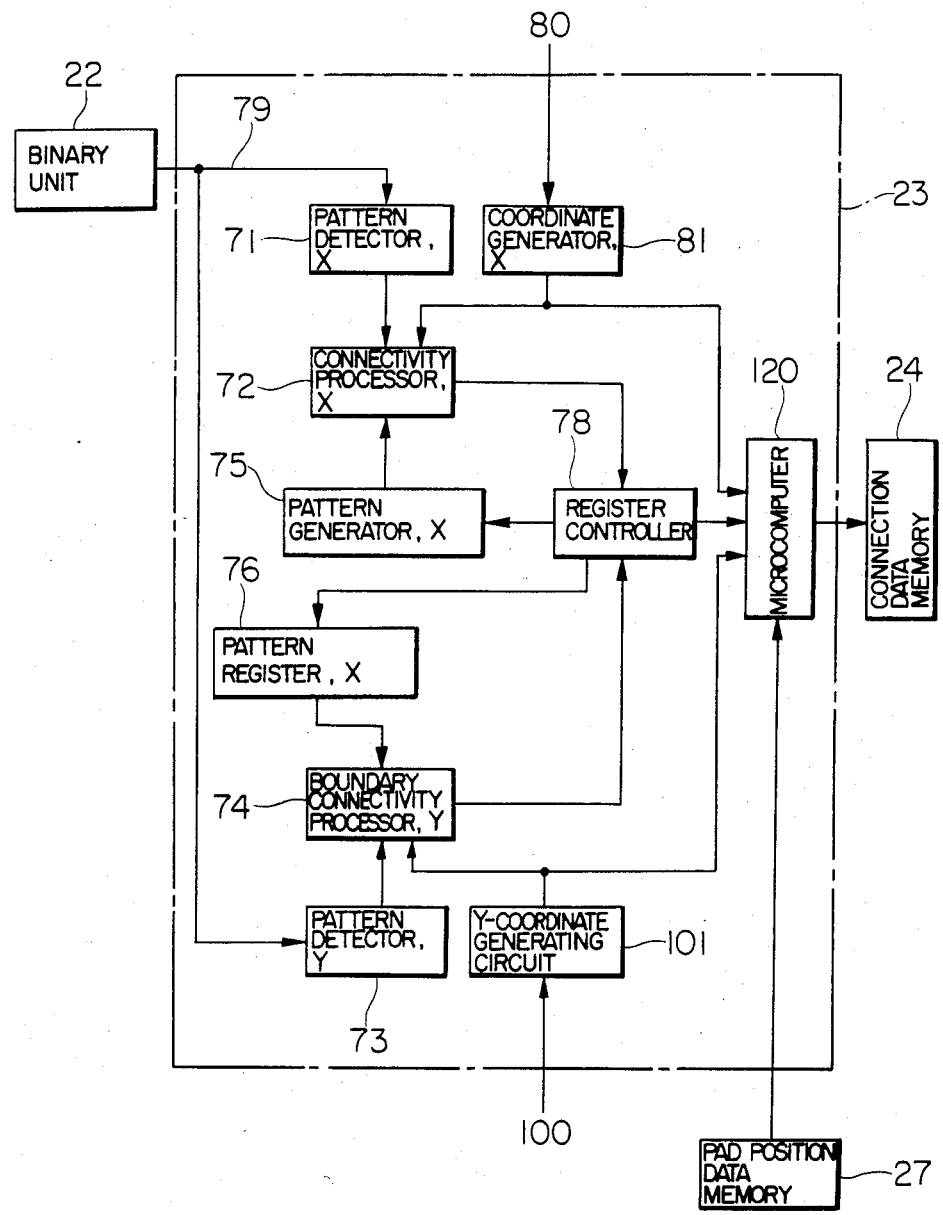
FIG. 10 is a general block diagram showing one embodiment of the image processing system according to the present invention.
Figure 11:
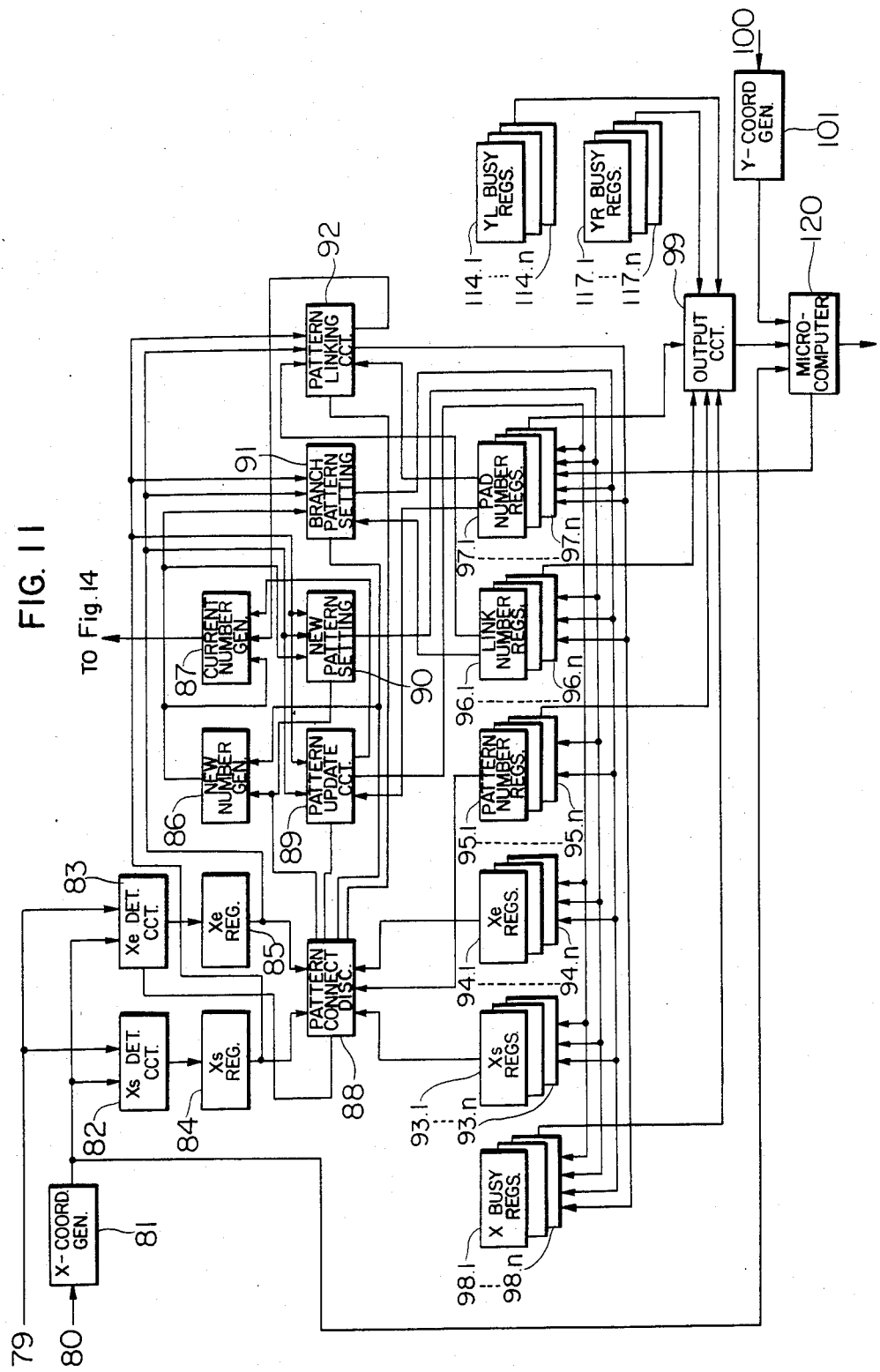
FIG. 11 is a block diagram showing in detail the X-direction connectivity processor shown in FIG. 10.

FIG. 11 is a block diagram showing in detail the portions of the arrangement shown in FIG. 10 for carrying out the connectivity process for the X-axis direction, including the X-axis pattern detector 71, X-axis pattern connectivity processor 72, X-axis pattern generator 75, pad number register 77, and register controller 78. The arrangement of FIG. 11 receiving the binary signal 79 and X-axis scanning clock 80 includes an X-coordinate generator 81, an Xs detection circuit 82 for detecting the pattern start point Xs, ar Xe detection circuit 83 for detecting the pattern end point Xe, Xs and Xe registers 84 and 85 for storing the current values of Xs and Xe, a new pattern number generator 86 for storing a new pattern number, a current pattern number register 87 for storing the current value of the pattern number, a pattern connectivity discrimination circuit 88, a pattern update circuit 89, a new pattern setting circuit 90, a branch pattern setting circuit 91, a pattern linking circuit 92, Xs registers 93-1 through 93-n for storing pattern information on the previous scanning line in the X direction, Xe registers 94-1 through 94-n, pattern number registers 95-1 through 95-n, link number registers 96-1 through 96-n, pad number registers 97-1 through 97-n, Xbusy registers 98-1 through 98-n for recording whether or not pattern information with each pattern number has changed in the current scanning in the X direction, and an output circuit 99 for providing the relation between the connectivity and the pad number. The Xs and Xe are the pattern start point and end point which appear sequentially on the scanning line in the X direction as exemplified in FIG. 12, and numbers 1 through n appended to the registers as 93-1 through 93-n and 98-1 through 98-n imply registers corresponding to the pattern numbers 1 through n.

Figure 12:
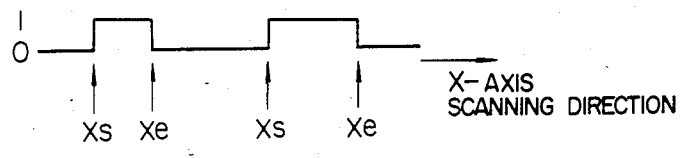
FIG. 12 is a waveform diagram used to explain the start point Xs and end point Xe of scanning in the X direction in the operation of the arrangement shown in FIG. 10.
Figure 13A:
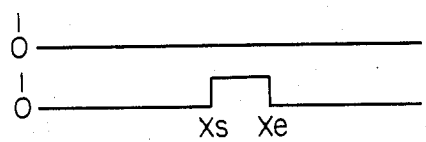
FIGS. 13A-13E are waveform diagrams used to explain the categories of the linkage relationship between the pattern on the previous scanning line and the pattern on the present scanning line.
Figure 13B:
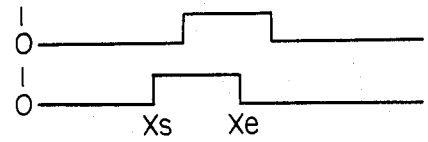
Figure 13C:
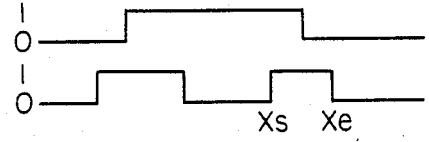
Figure 13D:
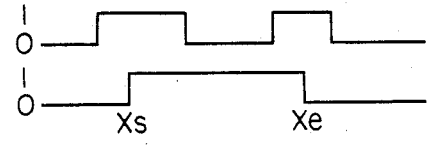
Figure 13E:
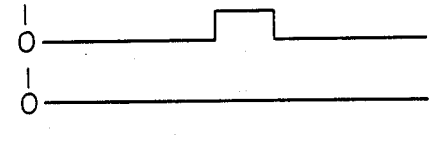

In this arrangement, the binary signal 79 of a field obtained from the image pickup unit through the binary digitizing circuit 22 is supplied to the Xs and Xe detection circuits 82 and 83 together with the X-coordinate signal produced by the X-coordinate generating circuit 81 in response to the X-axis scanning clock 80. Then, the Xs and Xe detection circuits 82 and 83 detect the pattern start point Xs and end point Xe on the scanning line as shown in FIG. 12, and store the coordinate values in the Xs and Xe registers 84 and 85. The pattern connectivity discrimination circuit 88 is activated in response to the detection of the end point Xe, and the circuit 88 compares the start point Xs and end point Xe of the current pattern provided by the Xs and Xe registers 84 and 85 with Xs and Xe from ones of the Xs registers 93-1 through 93-n and Xe registers 94-1 through 94-n for storing Xs and Xe of each pattern on the previous scanning line. In this case, the linkage relationship between the current pattern of Xs and Xe detected on the scanning line and the pattern on the previous scanning line can be classified into five modes as shown in FIGS. 13A–13E. In FIG. 13A, the current pattern is a newly detected pattern, and it will be called "new pattern". In FIG. 13B, the current pattern links with a pattern on the previous scanning line, and it will be called "single linkage". In FIG. 13C, the current pattern links with a pattern on the previous scanning line, the latter pattern being in linkage with an old pattern on the current scanning line, and it will be called "branching". In FIG. 13D, the current pattern links with more than one pattern on the previous scanning line, and it will be called "multi-linkage". In FIG. 13E, no pattern in linkage on the previous scanning line has been detected at the end of the current scanning line, and it will be called "ending".

The connectivity discrimination circuit 88 compares Xs and Xe of the above-mentioned current pattern with Xs and Xe of each pattern on the previous scanning line so as to identify the linkage mode and activates a circuit corresponding to the linkage mode. At each starting of X-axis scanning, the Xbusy registers 98-1 through 98-n are cleared.

First, in the new pattern mode shown in FIG. 13A, the contents of the new pattern number register 86 are incremented by 1 so that a pattern number which has been stored is replaced with the pattern number of a new pattern. At the same time, the new pattern setting circuit 90 is activated, and the contents of the new pattern number register 86 are transferred to the current pattern number register 87. Based on the new pattern number (assumed to be m) in the new pattern number register 86 and the values of Xs and Xe of the new pattern in the Xs and Xe registers 84 and 85 for storing the current values of Xs and Xe, the new pattern setting circuit 90 loads the Xs register 93-m with Xs, the Xe register 94-m with Xe, the pattern number register 95-m with m, the link number register 96-m with m, the pad number register 97-m with the value of the pad number in response to the command from the microcomputer 120 when the scanning position coincides with the pad coordinates stored in the pad position data memory 27, and the Xbusy register 98-m with 1 (busy).

In the single linkage mode shown in FIG. 13B, the pattern update circuit 89 is activated and it is informed as to which one of the patterns with pattern numbers 1 through n on the previous scanning line (assumed to be one with pattern number l) the current pattern links with. The pattern update circuit 89 loads the pad number register 97-l with the pattern number l and, if the pad is detected by the microcomputer 120, the pad number, the Xs register 93-l with Xw, the Xe register 94-l with Xe, the Xbusy register 98-l with 1, and the current pattern number register 87 with pattern number l.

In the branching mode shown in FIG. 13C, the branch pattern setting circuit 91 is activated, and it is informed as to which one of the patterns with pattern numbers 1 through n (assumed to be one with pattern number k) the current pattern links with, then the contents of the new pattern register are incremented by 1 (the new pattern number is assumed to be m'). The branch pattern setting circuit 91 loads the Xs register 93-m' with Xs, the Xe register 94-m' with Xe, the pattern number register 95-m' with m', the pad number register 97-m' with a pad number if a pad is detected by the microcomputer 120, and the link number register 96-m' with a value which is read out from the link number register 96-k.

In the multi-linkage mode shown in FIG. 13D, the pattern linkage circuit 92 is activated and the pattern numbers of patterns in linkage (assumed to be $j_1$ through $j_i$) are informed. The pattern linkage circuit 92 extracts the smallest pattern number, e.g., $j_k$, out of pattern numbers j through j and sets the pattern number $j_k$ as the current pattern number to the current pattern number register 87. At the same time, the pattern linkage circuit 92 reads the contents of the link number register 6-$j_k$ and loads link number registers 96-$j_l$ through 96-$j_i$ (excluding $j_k$) corresponding to pattern numbers $j_l$ through $j_i$ (excluding $j_k$) with the contents of the link number register 96-$j_k$, and further loads the Xs register 93-$j_k$ with Xs, and Xe register 94-$j_k$ with Xe, the Xbusy register with 1, and if a pad is detected by the microcomputer 120, the pad number register 97-$j_k$ with its pad number.

In the pattern ending mode shown in FIG. 13E, no operation takes place.

At the end of a scanning in the X direction, the circuit 99 for providing the relationship between the connectivity and the pad number has the same link number in the link number registers 96-1 through 96-n. A pattern with value 0 (not busy) in the Xbusy registers 98-1 through 98-n and value 0 (not busy) in the YLbusy registers 114-1 through 114-n and YRbusy registers 117-1 through 117-n, as will be described later, is searched, and if it exists, indicating that the connectivity process for that pattern has been completed, and its link number and pad number are sent to, for example, the microcomputer 120.

In the case of the connectivity process at the boundary of the upper and lower detection fields as shown in FIG. 8, the above-mentioned procedures are applied to the connectivity process for the pattern on the top X-axis scanning line in the next lower detection field B using Xs, Xe, pattern numbers, link numbers, pad numbers, and the contents of the Xbusy registers 93-1 through 93-n, 94-1 through 94-n, 95-1 through 95-n, 96-1 through 96-n, 97-1 through 97-n, and 98-1 through 98-n for the bottom X-axis scanning line in the next higher detection field A, while using the above-mentioned X-axis connectivity process of FIG. 11, whereby the continuity at the boundary of the upper and lower detection fields can be preserved.

Figure 14:
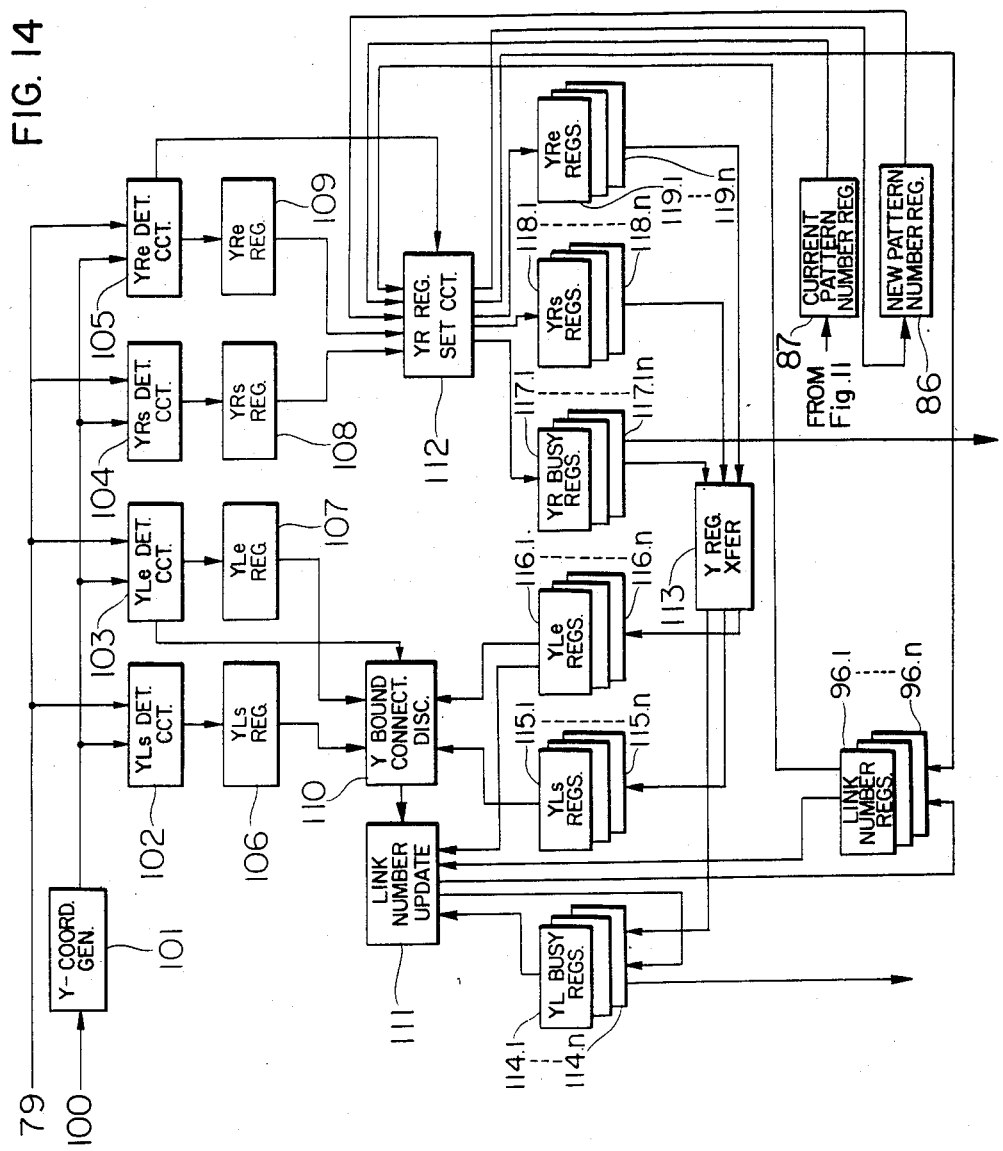
FIG. 14 is a block diagram showing in detail the Y-direction connectivity processor shown in FIG. 10.

FIG. 14 is a block diagram showing in detail part of the arrangement of FIG. 10 for carrying out the connectivity process in the Y direction at the boundary of the right-hand and left-hand detection fields as shown in FIG. 9, including a Y-axis pattern detector 73, a Y-axis boundary pattern connectivity processor 74, a Y-axis pattern register 76, and a register controller 78. The arrangement receiving the binary signal 79 and Y-axis clock 100 includes a Y-coordinate generating circuit 101, a YLs detection circuit 102 for detecting point YLs at which the pattern comes in contact with the left-hand boundary of the detection field, a YLe detection circuit 103 for detecting point YLe at which the pattern goes off the boundary, a YRs detection circuit 104 and YRe detection circuit 105 for detecting points YRs and YRe at which the pattern comes in contact with the right-hand boundary of the detection field and goes off the boundary, respectively, YLs, YLe, YRs and YRe registers 106–109 for storing values YLs, YLe, YRs and YRe of pattern information detected during the process on the boundary of the detection fields, a Y-axis boundary connectivity discrimination circuit 110, a link number update circuit 111, a YR register setting circuit 112 related to the Y-axis left-hand boundary, a YR register setting circuit 112 related to the X-axis left-hand boundary, a Y register transfer circuit 113 related to the Y-axis boundary, and YLbusy registers 114-1 through 114-n, YLs registers 115-1 through 115-n, YLe registers 116-1 through 116-n, YRbusy registers 117-1 through 117-n, YRs registers 118-1 through 118-n, YRe registers 119-1 through 119-n related to the Y-axis left-hand boundary and storing the values of YLs, YLe, YR, YRs, and YRe.

The new pattern number register 86, current pattern number register 87 and link number registers 96-1 through 96-n are used commonly by the arrangements of FIGS. 11 and 14.

Figure 15:
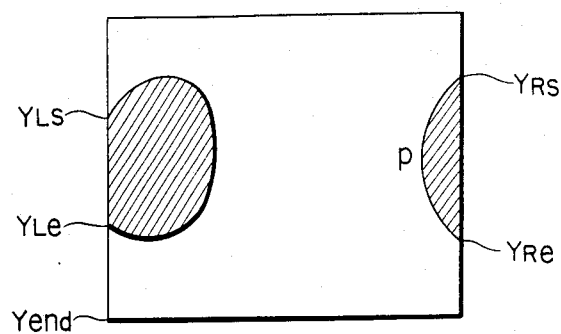
FIG. 15 is a plan view used to explain the left-hand pattern start point $Y_{Ls}$ and end point $Y_{Le}$ and the right-hand pattern start point $Y_{Rs}$ and end point $Y_{Re}$ at the boundary of the right-hand and left-hand detection fields in the operation of the arrangement shown in FIG. 14.
Figure 16:
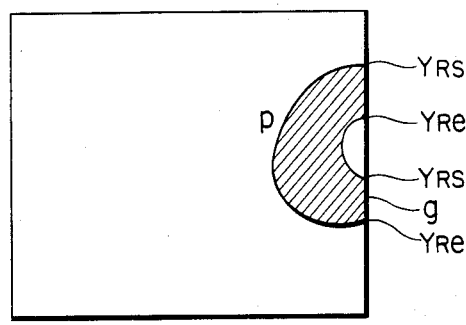
FIG. 16 is a plan view used to explain the status of a single pattern with a unique pattern number coming in contact with the right-hand field boundary more than once.

The Y-direction connectivity process performed by the above arrangement is to preserve the continuity of patterns having the left-hand start point YLs and end point YLe and the right-hand start point YRs and end point YRe, as shown in FIGS. 15 and 16, with the adjacent detection fields at the boundary of the right-hand and left-hand detection fields, and the process is conducted only for the first and last picture elements in scanning the detection field in the X direction. The binary signal 79 of the field is supplied together with the Y-coordinate signal which is derived from the Y-axis clock 100 and transformed to the Y-axis coordinate value by the Y-coordinate generating circuit 79, so that the YLs, YLe, YRs and YRe detection circuits 102–105 detect the values of YLs, YLe, YRs and YRe as shown in FIGS. 15 and 16 and load them to the YLs, YLe, YRs and YRe registers 106–109.

Subsequently, the connectivity process at the right-hand boundary of the detection field follows. In response to the detection of the end point YRe of the pattern at the right-hand boundary by the YRe detection circuit 105, the YR register setting circuit 112 is activated. The YR register setting circuit 112 makes reference to the current pattern number register 87 to know the pattern number of that pattern (assumed to be p) and checks whether the pattern start point YRs at the right-hand boundary is already set in the YRe register 118-p. If it is found that the YRs is not set, indicating that a pattern having a pattern number (p) as shown by the pattern at the right-hand boundary of FIG. 15 first comes in contact with the right-hand boundary, the YRs register 118-p is loaded with YRs, the YRe register 119-p with YRe, and the YRbusy register 117-p with 1. If, on the other hand, YRs is found to be set in the YRs register, indicating that a pattern having the same pattern number (p) is already located on the right-hand boundary as shown in FIG. 16, causing a pattern with one pattern number (p) to have more than one value for YRs and YRe. An imaginary pattern number (assumed to be q) is given to the boundary to set YRs and YRe in this location and, at the same time, the new pattern number register 86 is incremented by 1 so as to provide the link number of the pattern with pattern number p, and based on the value (q), the YRs register 118-q is loaded with YRs, the YRe register 119-q with YRe, the YRbusy register 117-q with 1, and the link number register 96-q with the value of the link number register 96-p. The YRbusy registers 117-1 through 117-n are cleared before processing the first detection field located top left. Thus, the Y-direction connectivity process at the right-hand boundary performs linking during the processes of detection fields from top to bottom. At a time when control is transferred to the process for the detection field located top right, the Y register transfer circuit 113 transfers the contents of the YRbusy registers 117-1 through 117-n to the YLbusy registers 114-1 through 114-n, the contents of the YRs registers 118-1 through 118-n to the YLs registers 115-1 through 115-n, and the contents of the YRe registers 119-1 through 119-n to the YLe registers 116-1 through 116-n, then clears the YRbusy registers 117-1 through 117-n, YRs registers 118-1 through 118-n, and YRe registers 119-1 through 119-n. That is, information of YRs, YRe and YRbusy on the right-hand boundary is used for the right-ajoining field as information of YLs, YLe and YLbusy on the left-hand boundary. Although the transfer of the contents of the YRs, YRe and YRbusy registers 118, 119 and 117 has been shown as an example, the arrangement may be made to switch the pointers of the registers instead of transferring the contents.

Figure 17:
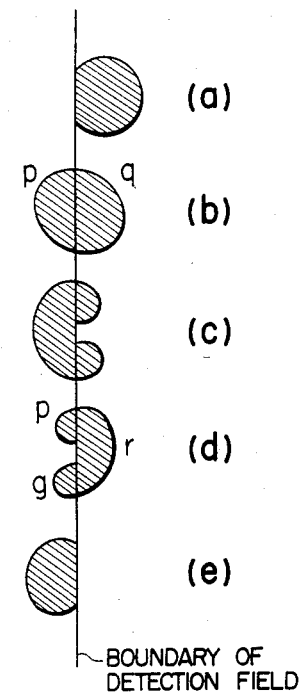
FIG. 17 is a set of partial plan views used to explain the categories of linkage relationship of a pattern lying on the boundary of the right-hand and left-hand Y-direction detection fields.

Next, the connectivity process at the left-hand boundary of the detection field will be explained. In response to the detection of the pattern end point YLe at the left-hand boundary by the YLe detection circuit 33, the Y-direction boundary connectivity discrimination circuit 110 is activated. The circuit 110 compares the values of the detected YLs and YLe with the values of YLs and YLe in the YLs registers 115-1 through 115-n and YLe registers 116-1 through 116-n which store pattern information obtained from the adjacent detection field which has been processed. In this case, the Y-direction linkage relationship between the pattern at the left-hand boundary of the detection field and the pattern at the right-hand boundary of the left-ajoining detection field which has been processed can be classified into five modes as shown in FIGS. 17 (a) through 17 (e). This classification is essentially identical to the classification of five linkage modes in the X-axis scanning detection described in connection with FIG. 13, and these modes of FIG. 17 will be called (a) new pattern, (b) single linkage, (c) branching, (d) multi-linkage, and (e) ending. The ending mode of (e) is not detected by the Y-direction boundary connectivity discrimination circuit 110, and the circuit 110 detects mode (a) or (d) and indicates the discrimination result together with the related information to the link number update circuit 111. If the mode is found to be a new pattern (a), the circuit 111 searches the YLe registers 116-1 through 116-n for the value of YLe smaller than the end point YLe of that pattern, and clears the corresponding YLbusy register 114. If, on the other hand, the mode is found to be single linkage (b), the circuit 111 compares the contents of the link number registers 96-p and 96-q, where p is the pattern number of the pattern in the left-ajoining detection field and q is the pattern number of the detected pattern on the right hand (see FIG. 17 (b)), and replace the larger value with the smaller value, then clears the YLbusy register 114 having YLe smaller than the end point YLe of the detected pattern. In the case of the branching mode (c), the process for the single linkage mode (b) is carried out each time the pattern end point YLe of each pattern on the right is detected. In the case of the multi-linkage mode (d), the link numbers of a plurality of patterns (e.g., pattern numbers p and q) of the left-ajoining detection field are compared with the link number of the pattern (pattern number r) detected on the right, and the smallest link number is set to the link number registers 96-p, 96-q and 96-r for a plurality of left-ajoining patterns and the detected pattern on the right, then the YLbusy register having YLe smaller than the end point YLe of the detected pattern is cleared. Furthermore, at a time when the operation reaches the bottom (assumed to be Yend) of one detection field, YL busy register 114 having YLe smaller than Yend is cleared. Through the processes described above, a pattern across the boundary of right-hand and left-hand detection fields is given the same link number, so that the continuity at the boundary is preserved.

The pad position data memory 27 stores the pad position (coordinates) to the pad number in accordance with design data. During the scanning of the image pickup unit 21, when the X and Y coordinates provided by the X-coordinate generating circuit 81 and Y-coordinate generating circuit 101 coincide with the pad coordinates stored in the pad position data memory 27, the microcomputer 120 stores the corresponding pad numbers in pad number registers 97-1 through 97-n corresponding to the link number. It is assumed, for example, that pad numbers 101 through 108 exist in the image field as shown in FIG. 20. Through the connectivity process as described above, pad numbers 101 through 108 are stored in the pad number registers 97-1 through 97-n in correspondence to the pattern numbers a' through e' as follows.

a'—101, 102; b'—103; c'—104; d'—105, 106; e'—107, 108. The microcomputer 120 reads out the above data from the pad number registers 97-1 through 97-n, and since pads with the same pattern number are linked through a pattern, the following connection data is finally produced and stored in the connection data memory 24.

That is to say, 101—102, 103—103, 104—104, 105—106, and 107—108 are provided with mother pad numbers 101, 103, 104, 105, and 107, respectively.

On the other hand, design data is prepared in advance based on design information of the circuit patterns and stored in the design data memory 26. After connection data of all circuit patterns have been produced (after all circuit patterns have been taken by the image pickup unit), the processor 25 executes the foregoing algorithm of defect detection and stores attribute data in the attribute data memory 28 for the discrimination of defects.

Figure 18:
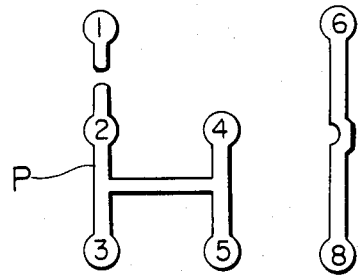
FIG. 18 is a plan view showing one example of patterns under test.
Figure 19:
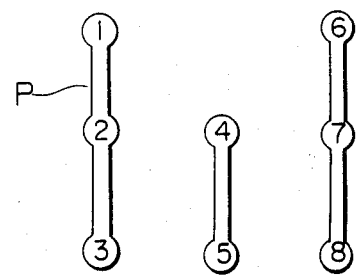

The following shows the process of defect defection using the example of circuit patterns under test shown in FIG. 18. Table 3 lists the connection data which is stored in the connection data memory 24 after the binary digitizing process and connectivity process have been conducted. Table 4 lists the design data for the normal circuit patterns shown in FIG. 19. In Table 4, the first column from the left hand side contains the address, the second column contains the pad number (pointer) of design data counted circularly from the second pad, the third column contains attribute data, and the fourth column contains the discrimination result. Attribute data is initialized to zero. First, the examination for the leading data in the connection data memory 24 shows that both pad numbers on the right and left in Table 3 are 1, and then 1 is set to the attribute data with address 1 in design data.

TABLE 3

| Object pad | Mother pad |
| --- | --- |
| 1 | 1 |
| 2 | 2 |
| 3 | 2 |
| 4 | 2 |
| 5 | 2 |
| 6 | 6 |
| 8 | 6 |

TABLE 4

| Address | Pad number | Attribute data | Discrimination result |
| --- | --- | --- | --- |
| 1 | 2 | 1 | Line |
| 2 | 3 | 1 | breakage |
| 3 | 1 | 2 | |
| 4 | 5 | 3 | Short-circuit |
| 5 | 4 | 3 | |
| 6 | 7 | 1 | No pad |
| 7 | 8 | 0 | |

TABLE 4-continued

| Address | Pad number | Attribute data | Discrimination result |
| --- | --- | --- | --- |
| 8 | 6 | 2 | |

The next connection data shows that both pad numbers on the right and left are 2, and then 1 is set to the attribute data with address 2 in design data. The next connection data shows that the left-hand pad number is 3, while the mother pad number is 2. First, data (pointer) of design data with address 3 is examined to find it being 1, and it does not coincide with the mother pad number 2. Then, the next data pointed by address 1 is examined, and data is 2 which coincides with the mother pad number, and then 2 is set to the attribute data of address 3. The next connection data shows the left-hand pad number of 4 and the mother pad number of 2. Design data with address 4 is examined to find it being 5 which does not coincide with the mother pad number 2. Then, data of address 5 is examined to find it being 4 which does not coincide with the mother pad number 2 and, moreover, the data coincides with the left-hand pad number 4 in connection data, indicating that the pertinent mother pad has not been found throughout the circulation list. Then, attribute data of address 4 is made 3. Also for the next connection data, the mother pad is not found in the circulation list, and attribute data of address 5 is made 3. The next connection data shows that the left-hand pad number is 6 and the mother pad number is 6, and 1 is set to attribute data of address 6. The next connection data shows that the left-hand pad number is 8 and the mother pad number is 6, and data with address 8 in design data is examined to find it being 6, then 2 is set to the attribute data with address 8. And the attribute data of address 7 holds the initial value 0. The search of all connection data has been completed and attribute data has been produced.

The next procedure is to examine the attribute data for each circulation list for the discrimination of defects. First, for the patterns with pad numbers 1, 2 and 3 of design data, two attribute data indicate 1, and they are determined to be line breakage. For the pattern with pad numbers 4 and 5 of design data, both attribute data indicate 3, and it is determined to be short-circuiting another pattern. For the patterns with pad numbers 6, 7 and 8 of design data, one attribute data indicates 0, and a missing pad (pad number 7) is detected. Thus, the discrimination result points out the defects of the circuit patterns correctly. Although a short-circuit of patterns is detected in the discrimination result from only one side (the oattern with pad numbers 4 and 5) of design data, it cannot be a serious disadvantage. According to this embodiment. the short-circuit and line breakaqe can be detected in a non-contact manner using a relatively simple system arrangement.

Figure 23:
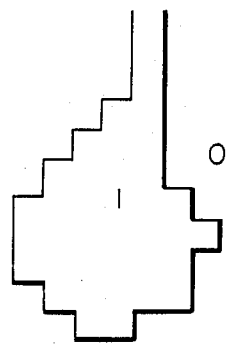
FIG. 23 is an illustration showing a pattern obtained through the contraction process for the pattern shown in FIG. 22.

Next, the second embodiment of the present invention will be described. FIG. 20 shows the system arrangement for carrying out this embodiment. This arrangement differs from that of the previous embodiment (shown in FIG. 4) in that a contraction processor 29 is inserted between the binarv digitizing circuit 22 and the connectivity processor 23, and the remaining portions are exactly the same. FIG. 21 shows one embodiment of the contraction processor 29. The processor consists of n-bit shift registers 31 of $m_2-1$ in number and $m_1$-bit shift registers 32 of $m_2$ in number. These shift registers are driven by a common sampling clock signal. The number n is equal to the number of sampling points in the horizontal direction of the image pickup unit 21, while the numbers $m_1$ and $m_2$ are determined depending on the sampling interval, the vertical resolution of the image pickup unit, and the size of defects to be detected. For example, when the sampling interval and vertical resolution are set equivalent to 10 $\mu$m and a defect of 30 $\mu$m square is to be detected, $m_1$ and $m_2$ are set to 3, and the arrangement becomes as shown in FIG. 21. The outputs of the $m_1$-by-$m_2$ bit shift registers 32 are combined by an AND gate 33, the output of which is delivered to the connectivity processor 23. While in FIG. 21 all shift register outputs are used, they may be used selectively depending on the shape of defects to be detected. FIG. 22 shows the original binary pattern, which is reduced to the pattern shown in FIG. 23 through the contraction process by the circuit of FIG. 21. A square with sides of unit length defines one picture element.

Figure 25:
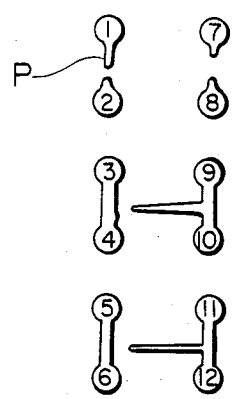
FIG. 25 is a plan view of patterns obtained through the contraction process for the pattern shown in FIG. 24.

FIG. 24 shows original patterns under test, which are reduced to the patterns shown in FIG. 25 through the contraction process. Table 5 lists connection data produced by the connectivity process for the patterns, and Table 6 lists the corresponding design data. Table 6 has additional columns on the right containing attribute data and the result of defect discrimination produced in the same way as in the first embodiment.

TABLE 5

| Object pad | Mother pad |
| --- | --- |
| 1 | 1 |
| 2 | 2 |
| 3 | 3 |
| 4 | 3 |
| 5 | 5 |
| 6 | 5 |
| 7 | 7 |
| 8 | 8 |
| 9 | 9 |
| 10 | 9 |
| 11 | 11 |
| 12 | 11 |

TABLE 6

| Address | Design data | Attribute data | Discrimination result |
| --- | --- | --- | --- |
| 1 | 2 | 1 | Line breakage |
| 2 | 1 | 1 | |
| 3 | 4 | 1 | Normal |
| 4 | 3 | 2 | |
| 5 | 6 | 1 | Normal |
| 6 | 5 | 2 | |
| 7 | 8 | 1 | Line breakage |
| 8 | 7 | 1 | |
| 9 | 10 | 1 | Normal |
| 10 | 9 | 2 | |
| 11 | 12 | 1 | Normal |
| 12 | 11 | 2 | |

As can be seen from the above result, a pattern width smaller than the specified value (30 $\mu$m in this example) can be detected as a line breakage. However, distinction between line breakages and extremelv narrow patterns is not possible, and small short-circuit sections can possibly be left undetected. Accordingly, this embodiment realizes a defective pattern detection system with a relatively simple arrangement for the application of defect detection without the need of distinction between line breakages and extremely narrow patterns.

Figure 26:
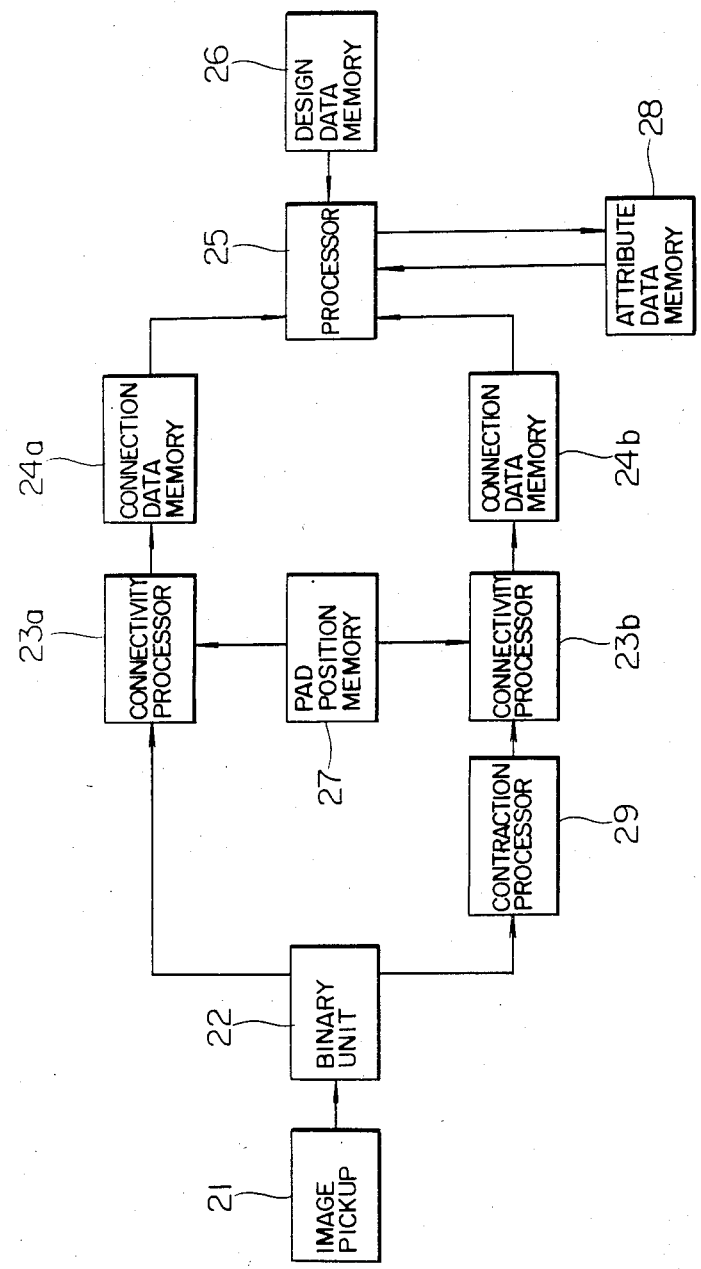
FIG. 26 is a block diagram showing the system arrangement for carrying out the third embodiment of the inventive method.

Next, the third embodiment of the present invention will be described. FIG. 26 shows the system arrangement for carrying out this embodiment. As can be seen from the figure, this embodiment is the combination of the first and second embodiments. Table 7 lists attribute data and the result of defect discrimination together with design data for the circuit patterns shown in FIG. 24.

TABLE 7

| Address | Design data | Attribute data | | Discrimination results | | |
|---|---|---|---|---|---|---|
| | | Original pattern | Contracted pattern | Original pattern | Contracted pattern | Total judgement |
| 1 | 2 | 1 | 1 | Normal | Line breakage | Narrow pattern |
| 2 | 1 | 2 | 1 | | | |
| 3 | 4 | 1 | 1 | Normal | Normal | Normal |
| 4 | 3 | 2 | 2 | | | |
| 5 | 6 | 1 | 1 | Normal | Normal | Normal |
| 6 | 5 | 2 | 2 | | | |
| 7 | 8 | 1 | 1 | Line breakage | Line breakage | Line breakage |
| 8 | 7 | 1 | 1 | | | |
| 9 | 10 | 3 | 1 | Short-circuit | Normal | Small Short-circuit |
| 10 | 9 | 3 | 2 | | | |
| 11 | 12 | 1 | 1 | Normal | Normal | Normal |
| 12 | 11 | 2 | 2 | | | |

The arrangement shown in FIG. 26 is the combination of the arrangements shown in FIGS. 4 and 20. The common reference numbers are given to the counterparts in these figures, and reference numbers suffixed by a indicate that the components belong to the system for processing the original patterns, while the reference numbers suffixed by b indicate that the components belong to the system for processing the contracted patterns. The processes conducted by both systems are exactly identical to those of the previous two embodiments, and in the final stage there is added a process of the total judgement on the discrimination results obtained from the original patterns and from the contracted patterns. In consequence, the use of two discrimination results allows distinction of line breakages and extremely narrow patterns and also prevents small short-circuit patterns from being undetected. Thus, this embodiment can detect line breakages and extremely narrow pattern sections distinctively.

Next, the fourth embodiment of the present invention will be described. FIG. 27 shows the system arrangement for carrying out this embodiment. The arrangement differs from that of the first embodiment shown in FIG. 4 in that an expansion processor 30 is inserted between the binary digitizing circuit 22 and the connectivity processor 23, and the remaining portions are exactly the same as before. FIG. 28 shows an embodiment of the expansion processor 30. The processor consists of n-bit shift registers 31 of $m_2-1$ in number and $m_1$-bit shift registers 32 of $m_2$ in number. These shift registers are driven by a common sampling clock signal. The number n is set equal to the number of sampling points in the horizontal direction of the image pickup unit, and the numbers $m_1$ and $m_2$ are determined depending on the sampling interval, the vertical resolution of the image pickup unit 21, and the size of defects to be detected. For example, when the sampling interval and vertical resolution are set equivalent to 10 μm and a defect of 30 μm square is to be detected, $m_1$ and $m_2$ are set to 3, and the circuit arrangement becomes as shown in FIG. 28. The outputs of the $m_1$-by-$m_2$ bit shift registers 32 are combined by an OR gate 34, the output of which is delivered to the connectivity processor 23. Although in FIG. 28 all shift register outputs are used, they may be used selectively depending on the shape of defects to be detected. FIG. 29 shows the result of the expansion process conducted by the processor of FIG. 28 for the binary pattern shown in FIG. 22. FIG. 30 shows circuit patterns as a result of the expansion process for the circuit patterns under test shown in FIG. 24, and Table 8 lists connection data produced through the connectivity process for the patterns. Table 9 lists attribute data and the defect discrimination result together with design data produced in the same way as in the first embodiment.

TABLE 8

| Connection data | Address |
|---|---|
| 1 | 1 |
| 2 | 2 |
| 3 | 3 |
| 3 | 4 |
| 5 | 5 |
| 5 | 6 |
| 7 | 7 |
| 7 | 8 |
| 3 | 9 |
| 3 | 10 |
| 5 | 11 |
| 5 | 12 |

TABLE 9

| Address | Design data | Attribute data | Discrimination result |
|---|---|---|---|
| 1 | 2 | 1 | Normal |
| 2 | 1 | 2 | |
| 3 | 4 | 1 | Normal |
| 4 | 3 | 2 | |
| 5 | 6 | 1 | Normal |
| 6 | 5 | 2 | |
| 7 | 8 | 1 | Normal |
| 8 | 7 | 2 | |
| 9 | 10 | 3 | Short-circuit |
| 10 | 9 | 3 | |
| 11 | 12 | 3 | Short-circuit |
| 12 | 11 | 3 | |

As can be seen from the result, spacings of patterns smaller than the specified value (30 μm in this example) can be detected as short-circuits. However, distinction between short-circuits and extremely small spacings of patterns is not possible, and small line breakages can possibly be left undetected. Accordingly, this embodiment can realize a defective pattern detection system in a relatively simple arrangement for the application of detection without the need of distinction between short-circuits and extremely small spacings of patterns.

Next, the fifth embodiment of the present invention will be described. FIG. 31 shows the system arrangement for carrying out this embodiment. As can be seen from the figure, this embodiment is the combination of the first and fourth embodiments. Table 10 lists attribute data produced for the circuit patterns under test shown in FIG. 24 and the result of discrimination on defects. The arrangement of FIG. 31 is the combination of the arrangements shown in FIGS. 4 and 27. Common reference numbers are given to the counterparts in these figures, and reference numbers suffixed by a indicate that the components belong to the system for processing the original patterns as in the case of FIG. 26, while reference numbers suffixed by c indicate that the components belong to the system for processing the expanded patterns. The processes of both systems are exactly identical to those of the first and fourth embodiments, and in the final stage they are added by a process of the total judgement on the discrimination results obtained from the original patterns and from the expanded patterns. As shown in Table 10, the use of two discrimination results allows distinction between short-circuits and extremely small spacings of patterns, and prevents small line breakages from being left undetected. Thus, according to this embodiment, short-circuits and extremely small spacings of patterns can be detected distinctively.

crimination results obtained from the contracted patterns and from the expanded patterns. As shown in Table 12, the use of two discrimination results allows complete detection of defective patterns distinctively, except for the distinction between extremely small spacings of patterns and small short-circuits, and between extremely narrow pattern sections and the line breakages. Thus, according to this embodiment, defects of complete short-circuits, complete line breakages, extremely small spacings of patterns or small short-circuits, and extremely narrow pattern sections or small line breakages can be detected distinctively.

TABLE 11

| | | Attribute data | | Discrimination results | | |
|---|---|---|---|---|---|---|
| Address | Design data | Contracted pattern | Expanded pattern | Contracted pattern | Expanded pattern | Total judgement |
| 1 | 2 | 1 | 1 | Line breakage | Normal | Narrow pattern or small line breakage |
| 2 | 1 | 1 | 2 | | | |
| 3 | 4 | 1 | 1 | Normal | Normal | Normal |
| 4 | 3 | 2 | 2 | | | |
| 5 | 6 | 1 | 1 | Normal | Normal | Normal |
| 6 | 5 | 2 | 2 | | | |
| 7 | 8 | 1 | 1 | Line breakage | Normal | Narrow pattern or small line breakage |
| 8 | 7 | 1 | 2 | | | |
| 9 | 10 | 1 | 3 | Normal | Short-circuit | Small spacing or small short-circuit |
| 10 | 9 | 2 | 3 | | | |
| 11 | 12 | 1 | 3 | Normal | Short-circuit | Small spacing or small short-circuit |
| 12 | 11 | 2 | 3 | | | |

TABLE 12

| Discrimination from attribute Contracted pattern | Results data Expanded pattern | Total judgement (candidate defect) |
|---|---|---|
| Normal | Normal | Normal |
| Normal | Short-circuit | Small spacing or small short-circuit |
| Normal | Line breakage | Unidentified defect |
| Short-circuit | Normal | Composite defect or unidentified defect |
| Short-circuit | Short-circuit | Short-circuit |
| Short-circuit | Line breakage | Unidentified defect |
| Line breakage | Normal | Narrow pattern or small line breakage |
| Line breakage | Short-circuit | Composite defect or unidentified defect |
| Line breakage | Line breakage | Line breakage |

TABLE 10

| | | Attribute data | | Discrimination results | | |
|---|---|---|---|---|---|---|
| Address | Design data | Original pattern | Expanded pattern | Original pattern | Expanded pattern | Total judgement |
| 1 | 2 | 1 | 1 | Normal | Normal | Normal |
| 2 | 1 | 2 | 2 | | | |
| 3 | 4 | 1 | 1 | Normal | Normal | Normal |
| 4 | 3 | 2 | 2 | | | |
| 5 | 6 | 1 | 1 | Normal | Normal | Normal |
| 6 | 5 | 2 | 2 | | | |
| 7 | 8 | 1 | 1 | Line breakage | Normal | Small line breakage |
| 8 | 7 | 1 | 2 | | | |
| 9 | 10 | 3 | 3 | Short-circuit | Short-circuit | Short-circuit |
| 10 | 9 | 3 | 3 | | | |
| 11 | 12 | 1 | 3 | Normal | Short-circuit | Small spacing |
| 12 | 11 | 2 | 3 | | | |

Next, the sixth embodiment of the present invention will be described. FIG. 32 shows the system arrangement for carrying out this embodiment. As can be seen from the figure, this embodiment is the combination of the second and fourth embodiments. Table 11 lists attribute data produced from the circuit pattern under test shown in FIG. 24 and the result of defect discrimination together with design data. The processes to reach this result are exactly identical to those of the second and fourth embodiments, and in the final stage they are added by a process of the total judgement on the dis- Next, the seventh embodiment of the present invention will be described. FIG. 33 shows the system arrangement for carrying out this embodiment. As can be seen from the figure, this embodiment is the combination of the first, second, and fourth embodiments. Table 13 lists attribute data produced from the circuit patterns under test shown in FIG. 24 and the result of defect discrimination together with design data.

The quantity of attribute data, when expressed in 4 bits including spare codes, is:

$$4 \text{ bits} \times 256^2 = 262{,}144 \text{ bits}$$

TABLE 13

| Address | Design data | Attribute data | | | Discrimination results | | | |
|---|---|---|---|---|---|---|---|---|
| | | Original pattern | Contracted pattern | Expanded pattern | Original pattern | Contracted pattern | Expanded pattern | Total judgement |
| 1 | 2 | 1 | 1 | 1 | Normal | Line breakage | Normal | Narrow pattern |
| 2 | 1 | 2 | 1 | 2 | | | | |
| 3 | 4 | 1 | 1 | 1 | Normal | Normal | Normal | Normal |
| 4 | 3 | 2 | 2 | 2 | | | | |
| 5 | 6 | 1 | 1 | 1 | Normal | Normal | Normal | Normal |
| 6 | 5 | 2 | 2 | 2 | | | | |
| 7 | 8 | 1 | 1 | 1 | Line breakage | Line breakage | Normal | Small short-circuit |
| 8 | 7 | 1 | 1 | 2 | | | | |
| 9 | 10 | 3 | 1 | 3 | Short-circuit | Normal | Short-circuit | Small short-circuit |
| 10 | 9 | 3 | 2 | 3 | | | | |
| 11 | 12 | 1 | 1 | 3 | Normal | Normal | Short-circuit | Narrow pattern |
| 12 | 11 | 2 | 2 | 3 | | | | |

The processes to reach this result are exactly identical to those of the first, second and fourth embodiments, and in the final stage they are added by a process of the total judgement on the discrimination results obtained from the contracted pattern, expanded pattern and original pattern. As shown in Table 14, the use of three discrimination results allows the complete detection of complete line breakages, complete short-circuits, small line breakages, small short-circuits, extremely narrow pattern sections, and extremely small spacings of patterns distinctively. Thus, according to this embodiment, detection of defects with the complete distinction of the type of defect is made possible.

TABLE 14

| Discrimination results based on attribute data | | | Total judgement |
|---|---|---|---|
| Original pattern | Contracted pattern | Expanded pattern | (candidate defect) |
| Normal | Normal | Normal | Normal |
| Normal | Normal | Short-circuit | Small spacing |
| Short-circuit | Normal | Short-circuit | Small short-circuit |
| Short-circuit | Short-circuit | Short-circuit | Short-circuit |
| Normal | Line breakage | Normal | Narrow pattern |
| Line breakage | Line breakage | Normal | Small line breakage |
| Line breakage | Line breakage | Line breakage | Line breakage |
| | Other than above | | Composite defect or unidentified defect |

The following will discuss the capacity of memory and processing time needed for the foregoing seven embodiments. First, the memory capacity will be calculated on assumption that a printed circuit board has 256-by-256 points of pads on it. In this case, the pad number can be expressed using a 16-bit (2 bytes) word. Assuming that all pads have been detected in the connectivity process, the quantity of connection data produced are:

$$(16 \text{ bits} + 16 \text{ bits}) \times 256^2 = 2{,}097{,}152 \text{ bits}$$

$$= 262.144 \text{ kbytes}$$

The quantity of design data is:

$$16 \text{ bits} \times 256^2 = 1{,}048{,}576 \text{ bits}$$

$$= 131.072 \text{ kbytes}$$

$$= 32{,}768 \text{ kbytes}$$

The total memory capacities calculated for the first through seventh embodiments are as follows.

First embodiment . . . 425.984 kbytes
Second embodiment . . . 425.984 kbytes
Third embodiment . . . 720.896 kbytes
Fourth embodiment . . . 425.984 kbytes
Fifth embodiment . . . 720.896 kbytes
Sixth embodiment . . . 720.896 kbytes
Seventh embodiment . . . 1,015.808 kbytes These memory capacities can be realized using 52–124 pieces of 64 kbit RAM device, and these values are quite practicable. When the ever increasing RAM density is taken into account, the number of memory devices can never be a worrying matter. For example, when comparing with 900M bits (112.5 Mbytes) of information of the original pattern image in inspecting a 150 mm square printed circuit board at a resolution of 5 μm, the scale of the memory capacity needed by the embodiments is by far small.

The processing time is estimated on the basis of the number of times of making reference to design data. For normal linked patterns having n pads on average, the mean value of the number of referencing design data for finding each mother pad in producing attribute data is calculated as follows.

$$\frac{\sum_{i=1}^{n} \{n - (i-1)\}}{n} = \frac{n+1}{2}$$

Accordingly, for a board including 256-by-256 pads, the number of reference operations is:

$$(n+1)/2 = 256^2$$

Assuming that 1% of all pads are involved in the defect of missing mother pad, the number of times of reference operation for this becomes from (n+1)/2 to n+1, and then:

$$\left\{ \frac{n+1}{2} \times 0.99 + (n+1) \times 0.01 \right\} \times 256^2 =$$

$$\left( \frac{n+1}{2} \times 256^2 \right) \times 1.01$$

Assuming n=4, design data is referenced 165,478.4 times for producing attribute data. The defect discrimination process needs the reference of all design data once, and then:

$$256^2 = 65,536 \text{ times}$$

The process by the image pickup unit 21 and to the generation of connection data by the connectivity processor 23 can be carried out on a real time basis. Accordingly, for the image pickup unit operating at a sampling frequency of 5 MHz and the microcomputer based processor which needs 100 μs for making reference to design data, the total inspection time needed for inspecting a 150 mm square board at the 5 μm resolution by each of the first through seventh embodiments is as follows.

First embodiment . . . 203.1 seconds
Second embodiment . . . 203.1 seconds
Third embodiment . . . 226.2 seconds
Fourth embodiment . . . 203.1 seconds
Fifth embodiment . . . 226.2 seconds
Sixth embodiment . . . 226.2 seconds
Seventh embodiment . . . 249.3 seconds According to the present invention, as described above, optical means are used to detect circuit patterns in a non-contact manner, and the linkage relationship between pads is obtained through the image process, whereby the fast and highly reliable pattern inspection without being affected by trivial deviations of circuit patterns under test and without damaging circuit patterns can be achieved. Particularly, the use of design data defining the linkage relationship in the form of list structure realizes the compression of data, for a board of 256-by-256 pads for example, from $256^2 \times 256^2 \approx 2.56 \times 10^9$ bits as in the case of using connection matrices to $1.05 \times 10^6$ bits, and at the same time processing time can also be reduced significantly.

Next, the apparatus to which the foregoing embodiments are applied will be described with reference to FIGS. 39 through 42. The embodiment shown in FIG. 39 is particularly suitable for the inspection of printed circuit patterns such as green sheet patterns. In the embodiment, a pattern P is formed on a white sheet which disperses the light (e.g., a green sheet mainly made of alumina) using black (or in a color darker than the sheet) metallic (e.g., tungsten) particles, and the shape of a pattern is formed into a binary signal without being affected by the bright spot noise.

The sheet is placed on a table 44 which is moved in the horizontal direction (x-y axes directions) by a motor 43, and illuminated by an illumination system including a mercury lamp 45, lamp power source 59, condenser lens 46, mirror 47, and filter 48 disposed right above the sheet. The light source is of course not limited to the mercury lamp 45, but other types of lamp such as a halogen lamp may be used, and in that case, the mirror 47 for changing the light path may not be used. The filter 48 is used for the purpose of cutting off the wavelength components which adversely affect the sheet, pattern material and the optical system. The provision of the filter is not an absolute requirement, but in many cases better results are obtained by use of a ultrared filter for avoiding the adverse effects of ultrared rays. In this case, the use of a cold mirror (ultrared transmitting mirror) for the mirror 47 provides still better effects. The image of the illuminated pattern is focused on two linear sensors 21a and 21b by focusing lenses 49a and 49b having the same magnification. The magnification is determined from the ratio of the necessary resolution of detection to the pitch of images on the linear sensors. The linear sensors 21a and 21b are disposed in such a way that optical images of the same magnitude can be detected and an image of the same position on the sheet is focused on both sensors 21a and 21b. The linear sensors 21a and 21b are arranged to have the same signal read-out direction (scanning direction) as shown by the arrows a1 and a2 in FIG. 39. These two linear sensors 21a and 21b are operated synchronously by a common sensor drive circuit 51. The analog image signals produced by the sensors are fed to amplifiers 52a and 52b, respectively, so that their d.c. offset and amplitude are corrected. Then, the signals are fed to shading correction circuits 53a and 53b by which the disparities of illumination and sensitivity of picture elements of the sensors are corrected. The shading correction circuits may be eliminated when the effects of the above-mentioned disparities are negligibly small. Among many types of shading correction circuits proposed, the circuits 53a and 53b are one, for example, disclosed in Japanese Patent Laid-open No. 57-35721. Next, the signals are transformed into binary signals using binary digitizing circuits 22a and 22b. Any of the fixed threshold method and floating threshold method may be employed. The binary signals are then combined using an AND gate 55, based on the assumption that the combined binary signal 79 has a positive polarity, i.e., a high level output represents a bright input to the sensor. If the circuits are arranged to provide a negative polarity signal, a NOR gate is used in place of the AND gate, and in this case a low signal level represents the pattern section of the image. The signal may be inverted using a NOT circuit.

A feed motor 43 for moving the table in the horizontal direction (x-y axes directions) is driven by a motor drive circuit 57, and its speed is determined depending on the scanning speed of the linear sensors, the reduction ratio of a ball-screw 57 and the resolution of detection in the feed direction.

The operation of the foregoing arrangement dealing with patterns shown in FIG. 38 will be described with reference to FIGS. 40A–40E and 40AA–40DD. FIGS. 40A and 40AA show the outputs of the linear sensors 21a and 21b, FIGS. 40B and 40BB show the outputs of the amplifiers 52a and 52b, FIGS. 40C and 40CC show the outputs of the shading correction circuits 53a and 53b, and FIGS. 40D and 40DD show the outputs of the binary digitizing circuits 22a and 22b. Among those, FIGS. 40A, 40B, 40C and 40D are for the signals produced along the line A1-A2 of FIG. 38B, while FIGS. 40AA, 40BB, 40CC and 40DD are for the signals produced along the line B1-B2 of FIG. 38C. Generally, the sensor outputs have different d.c. offsets and amplitudes as shown in FIGS. 40A and 40AA, they are equalized by using the amplifiers to obtain the signals as shown in FIGS. 40B and 40BB. The signals are fed through the shading correction circuits 53a and 53b so that the swell of the signals is removed, and then the signals are transformed into binary signals at threshold levels TH1 and TH2. Although in FIGS. 40C and 40CC the signals are shown in the analog form, they can be digital signals when the shading correction circuits 53a and 53b are so arranged. The digitizing system illustrated here is of a fixed threshold type, but it may be of a floating threshold type as will be described later. FIGS. 40D and 40DD show the binary signals obtained. Since the two sensors are arranged to detect exactly the same position of pattern as mentioned earlier, taking a logical product for the signals of FIGS. 40D and 40DD can eliminate bright spot noises to obtain the signal as shown in FIG. 40E. Thus, according to this embodiment, the binary image signal of circuit patterns without including bright spot noises can be obtained by a relatively simple arrangement. The use of linear sensors assures the dimensional accuracy in the directions of picture elements on both sensors, whereby the positioning adjustment for the sensors is simplified. This embodiment is applicable to black patterns on a white sheet, and for another case where patterns are formed of bright metallic particles on a dark sheet, the system for eliminating dark spot noises can readily be arranged by application of a modified version of this embodiment using an OR gate in place of the AND gate.

Next, the second embodiment of the inventive apparatus will be described with reference to FIG. 41. In the arrangement, the table movement system, illumination system and detection system are exactly identical to those of the previous embodiment. After the signal composing processes including amplification and shading correction are effected in exactly the same way as of the previous embodiment, a minimum selection circuit 60 provides the smaller of the two signals. This signal is outputted as a luminance image signal 61 of a pattern with bright spot noises being eliminated. The signal is, at the same time, digitized by a binary digitizing circuit 22 so that the binary signal 79 for the pattern is produced. The binary digitizing circuit 22 may be of the fixed threshold type or floating threshold type as mentioned above.

Figure 42A:
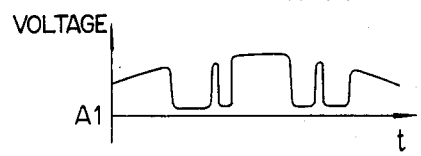
Figure 42A:
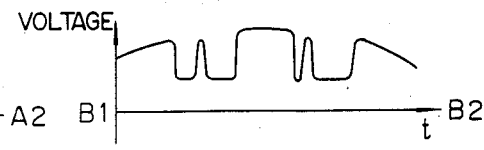
Figure 42B:
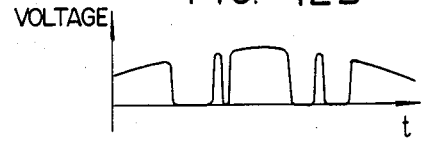
Figure 42B:
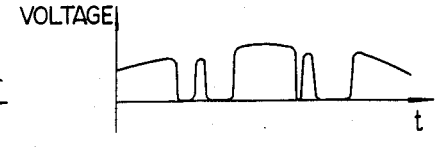
Figure 42C:
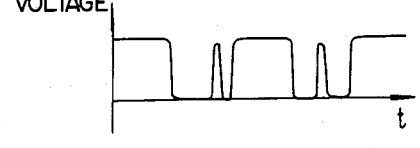
Figure 42C:
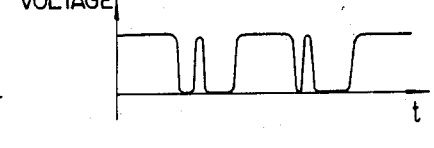
Figure 42D:
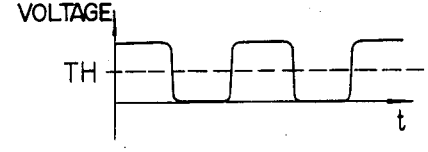
Figure 42E:
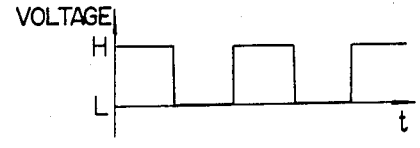

The operation of this embodiment will be described with reference to FIGS. 42A-42E and 42AA-42CC illustrating the waveforms of signals at various portions for the circuit patterns shown in FIG. 38. FIGS. 42A and 42AA show the outputs of the sensors 21a and 21b, FIGS. 42B and 42BB show the outputs of the amplifiers 52a and 52b, FIGS. 42C and 42CC show the outputs of the shading correction circuits 53a and 53b, FIG. 42D shows the output of the minimum selection circuit 62, and FIG. 42E shows the output of the binary digitizing circuit 22. The signals of FIGS. 42A, 42B and 42C are produced along the line A1-A2 on the patterns shown in FIG. 38B, while the signals of FIGS. 42AA, 42BB and 42CC are produced along the line B1-B2 of FIG. 38C. The waveforms of FIGS. 42A, 42B, 42C, 42AA, 42BB, and 42CC result from exactly the same operations as explained in the previous embodiment in connection with FIG. 40. The waveform of FIG. 42D represents the output of the minimum selection circuit 60 which selects the smaller of the signals shown in FIGS. 42C and 42CC, and this is the luminance image signal for the patterns with bright spot noises being eliminated. Although the signal of FIG. 42D is illustrated as an analog signal, it can be a digital signal when the shading correction circuits are designed to provide digital signals for FIGS. 42C and 42CC as in the case of the previous embodiment. Then, the signal is fed through the digitizing circuit 22 which employs a fixed threshold level, and a binary signal shown in FIG. 42E is produced. The signal may be transformed into a binary signal using a floating threshold value as in the case of the previous embodiment.

This embodiment can also be modified to deal with patterns formed of bright metallic particles on a dark sheet as in the case of the previous embodiment, by replacement of the minimum selection circuit with a maximum selection circuit so that dark spot noises can be eliminated.

As an alternative of the sensors used in the above embodiments, galvanomirrors may be used to perform linear scanning for circuit patterns and scintillation tubes are used to produce image signals. In this case, due to very high sensitivity of the scintillation tube, a low intensity light source such as light emitting diodes can be used in place of the mercury lamp.

According to the present invention, as described above, the shape of a pattern formed of fine particles, such as metallic fine particles, having planes of normal reflection can be detected at a high immunity of noises, and thus the employment of the inventive system allows the inspection of printed circuit patterns at a very high reliability. The system is basically a modified version of the bright field illumination, allowing the detection of bright optical images, and thus fast pattern detection is made possible.

We claim:

1. A method of detecting a defect of a circuit pattern comprising the steps of:
   (a) converting an optical image of a circuit pattern into electrical image signals by using an image pickup means;
   (b) transforming said electrical image signals into binary signals of picture elements by using a binary unit;
   (c) providing a pad of said pattern represented by said binary signals of picture elements with a symbol forming an object pad number corresponding to an address of said pad when said pad is detected at the position of said address designated by a pad position memory;
   (d) examining the connectivity between pads thus provided with a symbol forming said object pad number by using a connectivity processor, thereby to provide a pad with a symbol forming a mother pad number representative of the same group to which said pad belongs if said pad is connected with the other pad, and to provide a pad with a symbol forming a mother pad number corresponding to the object pad number of said pad if said pad is not connected with the other pad;
   (e) generating connection data consisting of said object pad number and said mother pad number to represent connectivity of said pads;

(f) storing said connection data into a connection data memory;

(g) storing into a design data memory design data consisting of an address of a pad of said pattern and a pad number corresponding to another address of another pad of said pattern if said pad and said another pad are connected with each other; and (h) comparing said connection data with said design data by using a processor to produce attribute data on the basis of which defectiveness of the circuit pattern is determined.

2. A method according to claim 1, wherein a step of contraction process for the binary pattern is performed between steps (b) and (c).

3. A method according to claim 1, wherein a step of an expansion process for the binary signals is performed between steps (b) and (c).

4. A method according to claim 2, wherein determination of defectiveness of the circuit pattern is on the basis of made a determination result obtained through said contraction process and a determination result obtained without said contraction process.

5. A method according to claim 3, wherein determination of defectiveness of the pattern is on the basis of made a determination result obtained through said expansion process and a determination result obtained without said expansion process.

6. A method according to claim 1, wherein added steps of contraction process and expansion process for the binary signals are performed between steps (b) and (c), determination of defectiveness of the pattern being made on the basis of a determination result obtained through said contraction process and a determination result obtained through said expansion process.

7. A method according to claim 1, wherein added steps of contraction process and expansion process for the binary signals are performed between steps (b) and (c), determination of defectiveness of the pattern being made on the basis of a determination result obtained through said contraction process, a determination result obtained through said expansion process and a determination result obtained without said contraction and expansion processes.

8. A method according to claim 1, wherein said steps of (a) and (b) comprise the steps of producing electrical image signals using a pair of image pickup means which sense the same position of a pattern along optical axes of different directions, and a step of comprising pattern sections of said two electrical signals to form said binary signals, respectively.

9. A method according to claim 1, wherein said circuit pattern comprises a circuit pattern formed of metallic particles laid on a green sheet mainly made of alumina.

10. A method according to claim 8, wherein said circuit pattern comprises a circuit pattern formed of metallic particles laid on a green sheet mainly made of alumina.

11. An apparatus for detecting a defect of a circuit pattern comprising:

image pickup means which senses an optical image of a circuit pattern and provides an electrical image signal;

a binary digitizing circuit which transforms said electrical image signal into binary signals representing picture elements;

connection data generating means which examines the connectivity relationship between two selected points of the circuit pattern represented by said binary and produces connection data signals representative of a connectivity relationship expressed by a pair of symbols given to said points; and comparison means for comparing said connection data signals with design data signals expressed in the form of a circulation list of symbols given to points in connectivity relationship, whereby determination of defectiveness of the pattern is made based on the output of said comparison means.

12. An apparatus according to claim 11, wherein means for effecting a contraction process on the pattern represented by said binary signal is provided between said binary digitizing circuit and said connection data generating means, and means for switching between a mode of processing a contracting binary pattern signal through said contraction processor means or another mode of processing the binary pattern signal without said contraction processor means.

13. An apparatus according to claim 11, wherein means for effecting an expansion process on the pattern represented by said binary signal is provided between said binary digitizing circuit and said connection data generating means, and means for switching between a mode of processing an expansion binary pattern signal through said expansion processor means or another mode of processing the binary pattern signal without said expansion processor means.

14. An apparatus for detecting a defect of a circuit pattern comprising means for illuminating an object and means for transducing an optical image of said illuminated object into an electrical signal so as to detect a defect of a circuit pattern formed on a planar surface of said object, wherein said illumination means is disposed so that said object is illuminated on a side of the formation of said circuit pattern, and wherein said apparatus further comprises two sets of image pickup means which sense the same position of said illuminated pattern along optical axes of different directions on the side of pattern formation and transform luminance images of the circuit pattern into electrical signals, and means for composing pattern sections of said two electrical signals.

15. An apparatus according to claim 14, wherein said image pickup means comprise linear sensors.

16. An apparatus according to claim 14, wherein said composing means comprises means for transforming said two electrical signals into binary signals separately, and means for performing a logical operation on said binary signals.

17. An apparatus according to claim 14, wherein said composing means comprises means for providing a value corresponding to the larger of said two electrical signals.

18. An apparatus according to claim 11, wherein said image pickup means comprises two sets of image pickup means which sense a same position of a circuit pattern under test along optical axes in different directions on the side of pattern formation and transform luminance images of the pattern into electrical signals, and means for composing pattern sections of said two electrical signals.

19. An apparatus according to claim 14, wherein said composing means comprises means for providing a value corresponding to the smaller of said two electrical signals.

20. An apparatus for detecting a defect of a circuit pattern comprising:

image pickup means which senses an optical image of a circuit pattern and provides an electrical image signal;

a binary digitizing circuit which transforms said electrical image signal into binary signals representing picture elements;

expansion means connected to said binary digitizing circuit for effecting a expansion process on the pattern represented by said binary signals to produce expanded pattern signals;

first connection data generating means connected to said binary digitizing circuit for examining the connectivity relationship between two selected points of the circuit pattern represented by said binary signals and producing first connection data signals representative of a connectivity relationship for said points;

second connection data generating means connected to said expansion means for examining the connectivity relationship between said two selected points of the circuit pattern represented by said expansion pattern signals and producing second connection data signals representative of a connectivity relationship for said points; and comparison means for comparing said first and second connection data signals to design data signals for said two selected points for producing an output representing a determination of the defectiveness of the pattern based on said comparison.

21. An apparatus according to claim 20, further including contraction means connected to said binary digitizing circuit for effecting a contraction process on the pattern represented by said binary signals to produce contraction pattern signals;

third connection data generating means connected to said expansion means for examining the connectivity relationship between said two selected points of the circuit pattern represented by said expansion pattern signals and producing third connection data signals representative of a connectivity relationship for said points;

said comparison means comparing said first, second and third connection data signals to said design data signals to produce said output representing a determination of the defectiveness of the pattern.

22. An apparatus for detecting a defect of a circuit pattern comprising:

image pickup means which senses an optical image of a circuit pattern and provides an electrical image signal;

a binary digitizing circuit which transforms said electrical image signal into binary signals representing picture elements;

contraction means connected to said binary digitizing circuit for effecting a contraction process on the pattern represented by said binary signals to produce contraction pattern signals;

first connection data generating means connected to said binary digitizing circuit for examining the connectivity relationship between two selected points of the circuit pattern represented by said binary signals and producing first connection data signals representative of a connectivity relationship for said points;

second connection data generating means connected to said contraction means for examining the connectivity relationship between said two selected points of the circuit pattern represented by said contraction pattern sigals and producing second connection data signals representative of a connectivity relationship for said points; and comparison means for comparing said first and second connection data signals to design data signals for said two selected points for producing an output representing a determination of the defectiveness of the pattern based on said comparison.

* * * * *